(12) United States Patent
Kang et al.

(10) Patent No.: US 11,357,827 B2
(45) Date of Patent: *Jun. 14, 2022

(54) METHOD FOR PREVENTING OR TREATING INFLUENZA VIRUS INFECTION USING PHARMACEUTICAL COMPOSITION COMPRISING IMMUNOGLOBULIN FC-FUSED INTERLEUKIN-7 FUSION PROTEIN

(71) Applicant: GENEXINE, INC., Seongnam-si (KR)

(72) Inventors: Moon Cheol Kang, Pohang-si (KR);
Young Woo Choi, Pohang-si (KR);
Donghoon Choi, Yongin-si (KR);
Young Chul Sung, Seoul (KR)

(73) Assignee: Genexine, Inc., Seongnam-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/777,437

(22) PCT Filed: Nov. 30, 2016

(86) PCT No.: PCT/KR2016/013966
§ 371 (c)(1),
(2) Date: May 18, 2018

(87) PCT Pub. No.: WO2017/095140
PCT Pub. Date: Jun. 8, 2017

(65) Prior Publication Data
US 2018/0353573 A1    Dec. 13, 2018

Related U.S. Application Data

(60) Provisional application No. 62/263,262, filed on Dec. 4, 2015.

(51) Int. Cl.
*A61K 38/20*    (2006.01)
*A61K 47/68*    (2017.01)
*A61P 31/16*    (2006.01)
*A61K 9/00*    (2006.01)
*A61P 11/00*    (2006.01)

(52) U.S. Cl.
CPC ........ *A61K 38/2046* (2013.01); *A61K 9/0043* (2013.01); *A61K 47/68* (2017.08); *A61K 47/6813* (2017.08); *A61P 31/16* (2018.01); *A61P 11/00* (2018.01)

(58) Field of Classification Search
CPC ............ A61K 38/2046; A61K 47/6813; A61K 47/68; A61P 31/16
See application file for complete search history.

(56) References Cited

U.S. PATENT DOCUMENTS

| | | | |
|---|---|---|---|
| 5,093,242 A | 3/1992 | Bachmair et al. | |
| 6,153,380 A | 11/2000 | Nolan et al. | |
| 7,585,947 B2 | 9/2009 | Morre et al. | |
| 7,589,179 B2 | 9/2009 | Gillies et al. | |
| 8,153,114 B2 | 4/2012 | Morre et al. | |
| 10,208,099 B2 | 2/2019 | Yang et al. | |
| 2002/0127564 A1 | 9/2002 | Nolan | |
| 2005/0054054 A1* | 3/2005 | Foss | C07H 21/04 435/69.52 |
| 2005/0164352 A1* | 7/2005 | Lauder | C07K 14/5418 435/69.52 |
| 2005/0249701 A1 | 11/2005 | Morre et al. | |
| 2006/0141581 A1* | 6/2006 | Gillies | C07K 14/5418 435/69.52 |
| 2008/0206190 A1 | 8/2008 | Morre et al. | |
| 2008/0300188 A1* | 12/2008 | Yang | A61P 5/06 514/7.6 |
| 2010/0196312 A1 | 8/2010 | Morre et al. | |
| 2011/0243887 A1 | 10/2011 | Lauder et al. | |
| 2012/0016104 A1 | 1/2012 | Morre et al. | |
| 2013/0217864 A1 | 8/2013 | Cho et al. | |
| 2014/0178393 A1 | 6/2014 | Andres et al. | |
| 2014/0377218 A1 | 12/2014 | Morre et al. | |

FOREIGN PATENT DOCUMENTS

| | | |
|---|---|---|
| EP | 0 314 415 B1 | 8/1994 |
| EP | 0 877 752 B1 | 5/2003 |
| JP | 2-501618 A | 6/1990 |
| JP | 2501618 B2 | 5/1996 |
| JP | 2000-504220 A | 4/2000 |
| JP | 2001-509661 A | 7/2001 |
| JP | 2009-501543 A | 1/2009 |

(Continued)

OTHER PUBLICATIONS

Seo et al. Journal of Virology, 2014; 88(16):8998-9009 (Year: 2014).*
Bowie et al. Deciphering the Message in Protein Sequences: Tolerance to Amino Acid Substitutions. Science, 1990, 247:1306-1310 (Year: 1990).*
Lazar et al. Transforming Growth Factor ox: Mutation of Aspartic Acid 47 and Leucine 48 Results in Different Biological Activities. Mol. Cell. Biol., 8:1247-1252, 1988 (Year: 1988).*
Bork. Powers and Pitfalls in Sequence Analysis: The 70% Hurdle. Genome Research, 2000; 10:398-400 (Year: 2000).*
Bowie et al. Science, 1990, 247:1306-1310 (Year: 1990).*
Burgess et al. J. Cell Biol. 111:2129-2138, 1990 (Year: 1990).*
Lazar et al. Mol. Cell. Biol., 8:1247-1252, 1988 (Year: 1988).*
Bork. Genome Research, 2000; 10:398-400 (Year: 2000).*
Greenspan et al. 1999. Defining epitopes: It's not as easy as it seems; Nature Biotechnology, 17:936-937 (Year: 1999).*

(Continued)

*Primary Examiner* — Vanessa L. Ford
*Assistant Examiner* — Sandra Dillahunt
(74) *Attorney, Agent, or Firm* — Sterne, Kessler, Goldstein & Fox P.L.L.C.

(57) ABSTRACT

The present invention relates to a pharmaceutical composition comprising an interleukin-7 fusion protein to which an immunoglobulin Fc region has been fused for preventing or treating diseases caused by influenza virus A. The fusion protein comprising the immunoglobulin Fc region and IL-7 according to the present invention protects the body from infection due to influenza virus A and thus can treat diseases which can be caused by the virus.

8 Claims, 11 Drawing Sheets

Specification includes a Sequence Listing.

(56) References Cited

FOREIGN PATENT DOCUMENTS

| | | |
|---|---|---|
| JP | 2010-531134 A | 9/2010 |
| JP | 2014-147396 A | 8/2014 |
| JP | 2015-57392 A | 3/2015 |
| KR | 10-2006-0112673 A | 11/2006 |
| KR | 10-2009-0045953 A | 5/2009 |
| KR | 10-2012-0041139 A | 4/2012 |
| KR | 10-2014-0004802 A1 | 1/2014 |
| KR | 10-2017-0066265 A | 6/2017 |
| WO | 2005/021592 A2 | 3/2005 |
| WO | 2007/019232 A2 | 2/2007 |
| WO | 2009/101737 A1 | 8/2009 |
| WO | 2015/015516 A2 | 2/2015 |

OTHER PUBLICATIONS

Seo et al. Crucial roles of IL-7 in the development of T follicular helper cells and in the induction of humoral immunity. Journal of Virology, 2014; 88(16): 8998-9009 (Year: 2014).*

Yong Bok Seo, et al., "Crucial Roles of Interleukin-7 in the Development of T Follicular Helper Cells and in the Induction of Humoral Immunity", Journal of Virology, Aug. 2014, pp. 8998-9009, vol. 88, No. 16.

Moon Cheol Kang, et al., "Intranasal Introduction of Fc-Fused Interleukin-7 Provides Long-Lasting Prophylaxis against Lethal Influenza Virus Infection", Journal of Virology, Mar. 2016, pp. 2273-2284, vol. 90, No. 5.

International Search Report for PCT/KR2016/013966 dated Mar. 2, 2017 [PCT/ISA/210].

Nam, et al., "Marked enhancement of antigen-specific T-cell responses by IL-7-fused nonlytic, but not lytic, Fc as a genetic adjuvant", Eur. J. Immunol., 2010, vol. 40, pp. 351-358 (8 pages total).

Whisstock et al., "Prediction of protein function from protein sequence and structure", Quarterly Reviews of Biophysics, vol. 36, No. 3, 2003, pp. 307-340.

International Search Report dated Mar. 9, 2017, issued by the International Searching Authority in application No. PCT/KR2016/014127.

Fry et al.; "Interleukin-7: from bench to clinic"; Blood, Jun. 1, 2002 vol. 99, No. 11; pp. 3892-3904.

GenBank, "interleukin-7 [synthetic construct]", Accession No. AAB70834.1 (Sep. 21, 1997), total 1 page.

Heufler et al.; "Interleukin 7 Is Produced by Murine and Humane Keratinocytes"; J. Exp. Med.; The Rockefeller University Press; vol. 178; Sep. 1993; pp. 1109-1114.

International Preliminary Report on Patentability and Written Opinion of the International Searching Authority dated Dec. 12, 2017 for related PCT/KR2016/006214.

International Search Report for PCT/KR2016/006214 dated Aug. 25, 2016.

Kroncke et al.; "Human follicular dendritic cells and vascular cells produce interleukin-7: a potential role for interleukin-7 in the germinal center reaction"; Eur. J. Immunol. 1996. 26: 2541-2544.

Marc Pellegrini et al.; "IL-7 Engages Multiple Mechanisms to Overcome Chronic Viral Infection and Limit Organ Pathology"; Cell 144, 601-613, Feb. 18, 2011.

Muegge et al.; "Interleukin-7: A Cofactor for V(D)J Rearrangement of the T Cell Receptor β Gene"; Science; vol. 261; Jul. 2, 1993; pp. 93-95.

Nanjappa et al.; "Immunotherapeutic effects of IL-7 during a chronic viral infection in mice"; Blood, May 12, 2011 vol. 117, No. 19; pp. 5123-5132.

Patel et al.; "Treatment of progressive multifocal leukoencephalopathy and idiopathic CD41 lymphocytopenia"; J Antimicrob Chemother 2010; 65: 2489-2492; publication Oct. 20, 2010.

Pellegrini et al.; "Adjuvant IL-7 antagonizes multiple cellular and molecular inhibitory networks to enhance immunotherapies"; nature medicine; vol. 15; No. 5; May 2009; pp. 528-536, 819.

Mikayama et al Proc. Natl. Acad. Sci. USA (1993) vol. 90, pp. 10056-10060.

Voet et al Biochemistry John Wiley & Sons, Inc. (1990) pp. 126-128 and 228-234.

Rosenberg et al.; "IL-7 Administration to Humans Leads to Expansion of CD8+ and CD4+ Cells but a Relative Decrease of CD4+ T-Regulatory Cells"; National Institute of Health; NIH Public Access Author Manuscript; J Immunother: 2006; 39(3): 313-319.

Sawa et al.; "Hepatic Interleukin-7 Expression Regulates T Cell Responses"; Immunity 30, 447-457, Mar. 20, 2009.

Snyder et al.; "IL-7 in allogeneic transplant: Clinical promise and potential pitfalls"; Leukemia & Lymphoma, Jul. 2006; 47(7): 1222-1228.

Watanabe et al.; "Interleukin 7 Is Produced by Human Intestinal Epithelial Cells and Regulates the Proliferation of Intestinal Mucosal Lymphocytes"; J. Clin. Invest. vol. 95, Jun. 1995, pp. 2945-2953.

Bork, "Powers and Pitfalls in Sequence Analysis: The 70% Hurdle", Genome Research, vol. 10, pp. 398-400, 2000 (4 pages total).

European Patent Office; Communication dated May 15, 2019 in counterpart application No. 16807859.0.

European Patent Office; Search Report dated Dec. 19, 2018 issued in counterpart application No. 16 807 859.0.

International Search Report of PCT/KR2016/012495 dated Jan. 13, 2017.

Japanese Patent Office; Search Report dated Jan. 8, 2019 issued in counterpart application No. 2017-564121.

NCBI, PDB: 4C54_A (Feb. 5, 2014), "Chain A, Crystal Structure of Recombinant Human IgG4 Fc".

Maryam Fazeli et al., "Efficacy of HPV-16 E7 Based Vaccine in a TC-1 Tumoric Animal Model of Cervical Cancer", Cell Journal, vol. 12. No. 4, 2011, pp. 483-488 (6 pages total).

* cited by examiner

METHOD FOR PREVENTING OR TREATING INFLUENZA VIRUS INFECTION USING PHARMACEUTICAL COMPOSITION COMPRISING IMMUNOGLOBULIN FC-FUSED INTERLEUKIN-7 FUSION PROTEIN

CROSS REFERENCE TO RELATED APPLICATIONS

This application is a National Stage of International Application No. PCT/KR2016/013966, filed on Nov. 30, 2016, which claims priority from U.S. Provisional Application No. 62/263,262, filed on Dec. 4, 2015.

TECHNICAL FIELD

The present invention relates to a composition of a fusion protein comprising interleukin-7 for preventing or treating viral infection, and more particularly, to a pharmaceutical composition which can be used for preventing or treating influenza virus infection comprising an interleukin-7 fusion protein in which immunoglobulin Fc region is fused.

BACKGROUND ART

Influenza A virus (IAV) is a seasonal epidemic virus which threatens human health. Recently, it has been reported that avian IAV variants including H5N1 and H7N9 can cross-infect humans with higher mortality than other strains of human-infecting IAV. In case of the avian IAV variants, no human-to-human transmission has been reported, but new IAV variants are likely to occur in humans without pre-existing immunity to the viral variant, which is a risk factor for the outbreak of global epidemic (Taubenberger J K et al., 2010, *Public Health Rep* 125 Suppl 3:16-26).

Although vaccinations against influenza virus are conducted every year, such vaccines have problems such as low productivity and low efficacy. In other words, it is very difficult to timely produce vaccines against new antigens found in mutant viruses.

Antiviral drugs such as a neuraminidase inhibitor, influenza virus therapeutic agent, have been reported to slow the progression of complications. In particular, it has been reported that treatment with a neuraminidase inhibitor within 2 to 3 days after IAV infection is effective in treating IAV (Dunning J et al., 2014, *The Lancet infectious diseases* 14:1259-1270). However, owing to the emergence of new viral variants resistant to antiviral drugs, one antiviral drug alone cannot prevent or treat all viral infections. Therefore, an effective countermeasure for highly pathogenic IAVs is urgently needed.

Accordingly, the present inventors have endeavored to develop a therapeutic agent capable of effectively inducing an immune response in vivo regardless of the mutation of the virus, and as a result, have found that an interleukin-7-Fc fusion protein has an excellent effect for the prevention and treatment of highly pathogenic influenza virus to complete the present invention.

DISCLOSURE OF INVENTION

Technical Problem

An object of the present invention is to provide a composition for preventing or treating a disease caused by influenza virus.

Solution to Problem

In accordance with one object of the present invention, there is provided a pharmaceutical composition for preventing or treating a disease caused by influenza virus, comprising an interleukin-7 (IL-7) fusion protein in which immunoglobulin Fc region is fused.

In accordance with another object of the present invention, there is provided a method for preventing or treating a disease caused by influenza virus, comprising administering to an individual an interleukin-7 (IL-7) fusion protein in which immunoglobulin Fc region is fused and a pharmaceutically acceptable carrier.

Advantageous Effects of Invention

A fusion protein comprising immunoglobulin Fc region and IL-7 according to the present invention can control the immune system in the individual to protect human body from infection by influenza virus, and also, the fusion protein can control immune-related substances to treat a disease caused by the virus. Accordingly, it can be utilized as a new pharmaceutical composition which can replace the conventional antiviral vaccine.

BEST MODE FOR CARRYING OUT THE INVENTION

Figure 1A:
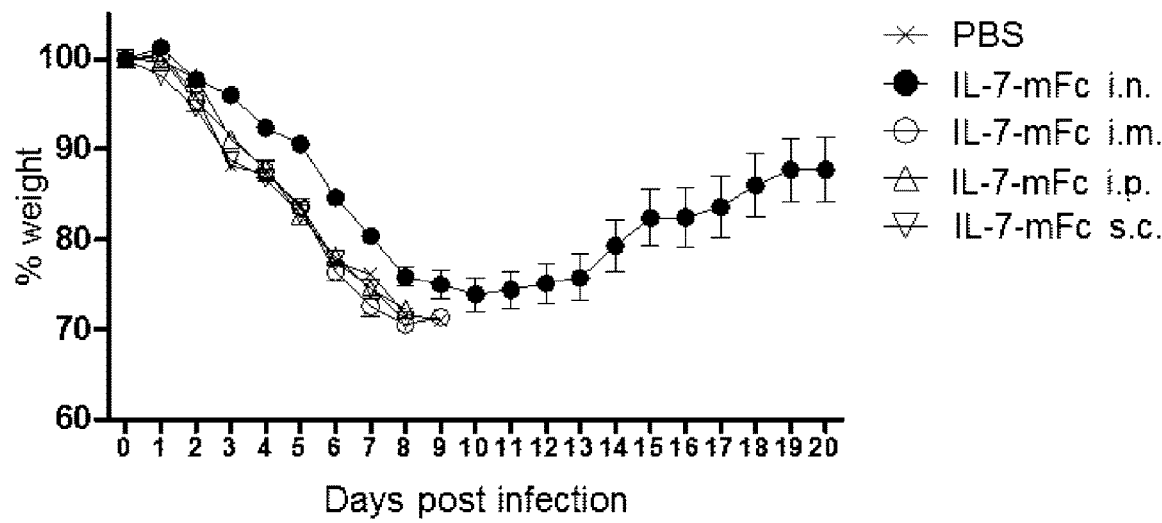
FIGS. 1a and 1b are graphs respectively showing weight change rate with respect to their initial body weight and survival rate of BALB/c mice depending on time passage after administration of IL-7-mFc through different routes.

In one aspect, the present invention provides a pharmaceutical composition for preventing or treating a disease caused by influenza virus, comprising an interleukin-7 (IL-7) fusion protein in which immunoglobulin Fc region is fused.

As used herein, the term "interleukin-7" may be a protein having the same amino acid sequence as interleukin-7 derived from an animal or a human. Further, the term "interleukin-7" may be a polypeptide or a protein having an activity similar to the interleukin-7 derived in vivo. Specifically, the IL-7 may be a protein comprising an IL-7 protein or a fragment thereof. Also, the IL-7 may be derived from a human, a rat, a mouse, a monkey, cattle or sheep.

The IL-7 comprises a polypeptide consisting of the amino acid sequences represented by SEQ ID NO: 1 to SEQ ID NO: 6. In addition, the IL-7 may have homology of about 70%, 75%, 80%, 85%, 90%, 91%, 92%, 93%, 94%, 95%, 96%, 97%, 98%, 99% or more to the sequences of SEQ ID NO: 1 to SEQ ID NO: 6.

Specifically, human IL-7 may have an amino acid sequence represented by SEQ ID NO: 1 (Genbank Accession No. P13232); rat IL-7 may have an amino acid sequence represented by SEQ ID NO: 2 (Genbank Accession No. P56478); mouse IL-7 may have an amino acid sequence represented by SEQ ID NO: 3 (Genbank Accession No. P10168); monkey IL-7 may have an amino acid sequence represented by SEQ ID NO: 4 (Genbank Accession No. NP_001279008); bovine IL-7 may have an amino acid sequence represented by SEQ ID NO: 5 (Genbank Accession No. P26895); and sheep IL-7 may have an amino acid sequence represented by SEQ ID NO: 6 (Genbank Accession No. Q28540).

In addition, the IL-7 protein or a fragment thereof may comprise a variety of modified proteins or peptides, i.e., variants. Such modification may be carried out by substitution, deletion or addition of one or more proteins of wild-type IL-7, which does not alter the function of IL-7. These various proteins or peptides may have homology of 70%, 75%, 80%, 85%, 90%, 91%, 92%, 93%, 94%, 95%, 96%, 97%, 98%, or 99% to a wild-type protein.

In general, substitution of a wild-type amino acid residue can be accomplished by substituting alanine or a conservative amino acid that does not affect the charge, polarity, or hydrophobicity of the entire protein.

The term "IL-7 protein" as used in the specification may be used as a concept including "IL-7 protein" and a fragment thereof. The terms "protein," "polypeptide," and "peptide" may be used interchangeably, unless otherwise specified.

In addition, the IL-7 may be a modified IL-7 having the following structure:

A-IL-7, wherein said A is an oligopeptide consisting of 1 to 10 amino acid residues, and the IL-7 is an interleukin-7 or a polypeptide having the activity similar to the interleukin-7.

Herein, said A may be directly linked to the N-terminus of the IL-7 or may be linked through a linker.

Said A may increase the productivity of IL-7 and may be prepared according to the method disclosed in Korean Patent Application No. 10-2016-0072769.

As used herein, said A may be linked to the N-terminus of IL-7. In the above formula, said A is characterized by containing 1 to 10 amino acids, which may be preferably selected from the group consisting of methionine, glycine, serine, and a combination thereof.

It is known that methionine and glycine do not induce an immune response in the human body. Although various protein therapeutic agents produced from E. coli necessarily contain methionine at the N-terminus thereof, no adverse immune effect has been reported. In the meantime, glycine is widely used in GS linker, and it is known that a commercial product such as Dulaglutide does not induce an immune response.

According to one embodiment, the oligopeptide A may be an oligopeptide comprising 1 to 10 amino acids selected from the group consisting of methionine (Met, M), glycine (Gly, G) and a combination thereof. Preferably, the oligopeptide A may be an oligopeptide consisting of 1 to 5 amino acids. For example, the oligopeptide A may be represented by the amino acid sequence selected from the group consisting of methionine, glycine, methionine-methionine, glycine-glycine, methionine-glycine, glycine-methionine, methionine-methionine-methionine, methionine-methionine-glycine, methionine-glycine-methionine, glycine-methionine-methionine, methionine-glycine-glycine, glycine-methionine-glycine, glycine-glycine-methionine, and glycine-glycine-glycine. Herein, the modified IL-7 may have any one of the amino acid sequences selected from SEQ ID NOS: 15 to 20.

Further, immunoglobulin Fc region may comprise an animal or human immunoglobulin Fc region, or a modified immunoglobulin Fc region thereof.

The IL-7 may be linked to the N-terminus or the C-terminus of the Fc region. It is known that even when IL-7 is fused to the C-terminus of the Fc region, IL-7 activity is maintained (U.S. Pat. No. 8,338,575 B2).

As used herein, the term "Fc region," "Fc fragment" or "Fc" refers to a protein which comprises heavy chain constant region 2 (CH2) and heavy chain constant region 3 (CH3) of immunoglobulin but does not comprise variable regions of heavy or light chain and light chain constant region 1 (CL1). It may further comprise a hinge region of the heavy chain constant region. Hybrid Fc or a hybrid Fc fragment may herein also be referred to as "hFc" or "hyFc." Also, as used herein, the term "a modified immunoglobulin Fc region" or "Fc region variant" refers to the Fc region in which one or more amino acids in the Fc region are substituted or the Fc region which is prepared by combining different Fc regions. Preferably, it refers to a Fc region whose binding force with a Fc receptor and/or a complement has been modified so as to exhibit weakened antibody-dependent cell-mediated cytotoxicity (ADCC) or complement dependent cytotoxicity (CDC) compared to the wild-type Fc region. The modified immunoglobulin Fc region can be selected from the group consisting of IgG1, IgG2, IgG3, IgD, IgG4, and a combination thereof.

In particular, the modified immunoglobulin Fc region comprises CH2 domain and CH3 domain in the N-terminus to C-terminus direction, wherein the CH2 domain comprises a portion of an amino acid residue of CH2 domain of human IgD and human IgG4, and the CH3 domain comprises a portion of an amino acid residue of human IgG4 CH3 domain.

The Fc region variant can be modified so as to increase the stability of the hinge region. Specifically, the 144$^{th}$ amino acid and/or the 145$^{th}$ amino acid of SEQ ID NO: 9 can be modified. Preferably, the variant may be a mutant in which K, the 144$^{th}$ amino acid of SEQ ID NO: 9, is substituted by G or S, and E, the 145$^{th}$ amino acid, is substituted by G or S.

In addition, the hFc can be represented by the following formula (I):

$$N'\text{-}(Z1)p\text{-}(Y)q\text{-}Z2\text{-}Z3\text{-}Z4\text{-}C', \quad \text{[Formula (I)]}$$

wherein,

N' is the N-terminus of a polypeptide and C' is the C-terminus of the polypeptide, p or q is an integer of 0 or 1, Z1 is an amino acid sequence having 5 to 9 consecutive amino acid residues in the N-terminus direction from the 98$^{th}$ position in the amino acid residues at 90$^{th}$ to 98$^{th}$ positions of SEQ ID NO: 7, Y is an amino acid sequence having 5 to 64 consecutive amino acid residues in the N-terminus direction from the 162$^{th}$ position in the amino acid residues at 99$^{th}$ to 162$^{nd}$ positions of SEQ ID NO: 7, Z2 is an amino acid sequence having 4 to 37 consecutive amino acid residues in the C-terminus direction from the 163$^{rd}$ position in the amino acid residue at positions 163$^{rd}$ to 199$^{th}$ in SEQ ID NO: 7, Z3 is an amino acid sequence having 71 to 106 consecutive amino acid residues in the N-terminus direction from the 220$^{th}$ position in the amino acid residues at 115$^{th}$ to 220$^{th}$ positions of SEQ ID NO: 8, and Z4 is an amino acid sequence having 80 to 107 amino acid residues in the C-terminus direction from the 221$^{st}$ position in the amino acid residues at 221$^{st}$ to 327$^{th}$ positions of SEQ ID NO: 8.

In addition, Fc fragment of the present invention may be a wild type sugar chain, an increased sugar chain compared with the wild type, a reduced sugar chain compared with the wild type, or a form in which the sugar chain is removed. The increase, reduction or removal of immunoglobulin Fc sugar chain can be carried out by a conventional method known in the art such as chemical method, enzymatic method and genetic engineering method using microorganisms. The removal of the sugar chain from Fc fragment rapidly reduces the binding affinity of the primary complement component C1 to C1q and results in a decrease or loss of ADCC (antibody-dependent cell-mediated cytotoxicity) or CDC (complement-dependent cytotoxicity), thereby not inducing unnecessary immune responses in vivo. In this regard, immunoglobulin Fc fragment in a deglycosylated or aglycosylated form may be more suitable for the purpose of the present invention as a carrier of a drug. As used herein, the term "deglycosylation" refers to enzymatical elimination of sugar from Fc fragment, and the term "aglycosylation" refers to the production of Fc fragment in an unglycosylated form by a prokaryote, preferably E. coli.

The modified immunoglobulin Fc region may comprise amino acid sequences of SEQ ID NO: 9 (hFc01), SEQ ID NO: 10 (hFc02), SEQ ID NO: 11 (hFc03), SEQ ID NO: 12 (hFc04) or SEQ ID NO: 13 (hFc05). In addition, the modified immunoglobulin Fc region may comprise the non-lytic mouse Fc of SEQ ID NO: 14.

According to the present invention, the modified immunoglobulin Fc region may be one described in U.S. Pat. No. 7,867,491, and the production of the modified immunoglobulin Fc region may be carried out with reference to the disclosure of U.S. Pat. No. 7,867,491.

In addition, the interleukin-7 fusion protein in which immunoglobulin Fc region is fused may have the amino acid sequence of any one of SEQ ID NOS: 21 to 27.

Meanwhile, the influenza virus may be Influenza A virus (IAV). In addition, the influenza A virus may have various kinds of H types and N types. The virus may specifically be one of 16 kinds of H subtypes and may be one of 9 kinds of N subtypes. For a specific example, the virus may be, but not limited to, H7N9, H5N1, H5N2, H3N2 or H1N1.

The interleukin-7 fusion protein in which immunoglobulin Fc region is fused according to the present invention may further comprise a pharmaceutically acceptable carrier. The pharmaceutically acceptable carrier may be any carrier that is suitable for being delivered to a patient and is non-toxic to the patient. Distilled water, alcohol, fats, waxes and inert solids may be included as carriers. Pharmacologically acceptable adjuvant (a buffer or a dispersant) may also be included in the pharmacological composition.

In another aspect of the present invention, there is provided a method for preventing or treating a disease caused by influenza virus, comprising administering to an individual an interleukin-7 (IL-7) fusion protein in which immunoglobulin Fc region is fused and a pharmaceutically acceptable carrier.

Herein, the method of administration to an individual may be a local administration, preferably intranasal administration. In case of that the composition of the present invention is provided topically, such as intranasal or aerosol administration, the composition preferably comprises a portion of an aqueous or physiologically compatible body fluid suspension or solution. Accordingly, the carrier or vehicle may be physiologically acceptable, and thus it can be added to the composition and delivered to the patient, which does not adversely affect the electrolyte and/or volume balance of the patient. Thus, a carrier for a formulation may generally include physiologic saline.

The method for preventing or treating a disease using a fusion protein of the present invention or a composition comprising the same may comprise administering another drug or physiologically active substance having the effect of preventing or treating a disease in combination with the protein or the composition of the present invention, while the route, timing, and dosage of the co-administration may be determined depending on the type of a disease, disease condition of a patient, the purpose of treatment or prevention, and other drug or physiologically active substance co-administered.

The isolated nucleic acid molecule encoding the modified interleukin-7 or a fusion protein comprising the same may encode a polypeptide having an amino acid sequence selected from the group consisting of SEQ ID NOS: 15 to 25. The nucleic acid molecule may comprise a polynucleotide sequence selected from the group consisting of SEQ ID NOS: 29 to 39. The nucleic acid molecule may further comprise a signal sequence or a leader sequence.

MODE FOR THE INVENTION

Hereinafter, the present invention will be described in more detail with reference to the following examples. However, the following examples are for illustrative purposes only and are not intended to limit the scope of the present invention.

Preparation Example 1: Preparation of Experimental Animals

BALB/c, BALB/c-nude, C57BL/6, and FcRn$^{-/-}$ mice used in the following examples were purchased from the Jackson Laboratory (Bar Harbor, Me., USA) and raised under specific pathogen-free conditions in an approved animal facility at POSTECH Biotech Center and International Vaccine institute (Seoul, Korea). All mouse experiments were performed in accordance with National Institutes of Health guidelines, and protocols were approved by the Institutional Animal Care and Use Committee (IACUC).

Preparation Example 2: Preparation of Mice and Antibody Administration Method

The murine non-lytic Fc fused IL-7 and non-lytic Fc fragment were prepared (Kim E S et al., 2013, *Nanoscale* 5:4262-4269). Recombinant human IL-7 (IL-7) used in the following examples was purchased from Shenandoah Biotechnology (Warwick, Pa., USA). A mixture of ketamine (100 mg/kg; Yuhan, Korea) and xylazine hydrochloride (10 mg/kg; Bayer, Belgium) in PBS was administered to the mice intraperitoneally to anesthetize, and then, 50 μl of PBS including predetermined cytokine was administered to the mice via indicated routes with a micropipette or syringe. The depletion monoclonal antibodies (mAbs) against mouse CD4 (GK1.5), CD8 (2.43), Vγ2 (UC3-10A6), and polyclonal rat IgG were purchased from Bioxcell (West Lebanon, N.H., USA). 200 μg of each depletion mAb was administered to the mice intraperitoneally at −1, 0, 1, and 4 days of post-IAV infection.

Preparation Example 3: Virus Infection and Titration

Influenza strains H1N1 (A/Puertorico/8/34) and H5N2 (A/aquatic bird/ma81/2007) used in the following examples were kindly provided by Young Ki Choi from Chungbuk National University of Medicine (Korea). Mice adapted to H5N2 were generated by passaging the H5N2 (A/Aquatic bird/Korea/W81/05) (Song M S et al., 2009, *Journal of virology* 83:12325-12335). At the predetermined time point after IL-7-mFc treatment, mice were anesthetized and infected intranasally with 3 $LD_{50}$ of PR8 or H5N2. Experiments using H1N1 (A/California/04/09) and H3N2 (A/Philippines/2/82) were performed with the aid of International Vaccine Institute (Korea). Body weight change and survival were monitored daily and groups with more than 50% of dead mice were excluded from the body weight graph. Mice that lose weight more than 30% with respect to their initial body weight were euthanized.

To measure virus titers, total lung homogenate samples of 3 and 7 days after infection, which were diluted 4 times with ten-fold serial dilution, were added to a monolayer of Madin-Darby canine kidney (MDCK) cells and the cytopathic effects were monitored daily. Virus titer was determined by a hemagglutinin test and calculated by the Reed and Muench method (Kim E H et al., 2013, *Virology journal* 10:104). Virus titer was described as $\log_{10}$ of the 50% tissue culture infective dose ($TCID_{50}$)/ml.

Preparation Example 4: BALF Collection and Lung Homogenate Preparation

The mice were anesthetized, and bronchoalveolar lavage fluid (BALF) was collected with 1 ml of PBS. After BALF collection, the lungs were collected and minced into small pieces and treated with type I collagenase (Gibco/Life Technology, Grand Island, N.Y., USA) and DNase I (Sigma-Aldrich, St. Louis, Mo., USA) at 37° C. for 30 to 45 min. Tissue fragments were harvested and crushed through a 70-μm strainer (BD Biosciences/Falcon™, San Jose, Calif., USA) to generate single cell suspensions. The cells were then washed and resuspended with RPMI-1640 (Welgene, Korea) containing 10% FBS (Hyclone, South Logan, Utah, USA), 2-mercaptoethanol (Gibco), and antibiotics (Gibco).

Preparation Example 5: Quantification of Cytokines, Chemokines, Influenza-Specific Antibodies and Total Proteins in the BALF and Sera The levels of cytokines and chemokines were first identified with a milliplex MAP mouse cytokine/chemokine kit (Millipore, Billerica, Mass., USA), and further analyzed using ELISA DuoSet kits (R&D systems, Minneapolis, Minn., USA) for mouse IFN-γ, IL-6, G-CSF, MCP-1, and IP-10 according to the manufacturer's protocol. Total protein concentrations in the BALF were measured using protein assay dye reagent (Bio-Rad, Hercules, Calif., USA) based on BSA (Roche, Germany) as a standard. To quantify the level of influenza-specific antibodies, total IgG and IgA were analyzed by direct ELISA with inactivated H5N2 virus. Total IgG-HRP and IgA-HRP were purchased from Southern Biotech (Birmingham, Ala., USA).

Preparation Example 6: Flow Cytometry

To prevent non-specific antibody binding, the single-cell suspensions of lung homogenate were incubated with Fc-blocker (2.4G2; eBioscience, San Diego, Calif., USA) in staining buffer (1% FBS in PBS). The cells were then stained with the following mAbs; mAbs against B220, CD3, CD4, CD8, CD11a, CD11b, CD11c, CD44, CD49d, CD62L, CD69, DX5, F4/80, Ly6C, MHC II, IFN-γ, TCRγδ, and 7-AAD (all from eBioscience); and mAbs against CD19, CD45, Gr-1, and Ly6G (all from BD Biosciences). For the intracellular cytokine staining of IFN-γ-producing CD8 T cells, lung homogenates were incubated for 6 hours with HA peptide (residue 529-543, Peptron, Korea), Brefeldin A (eBioscience) and DNase I (Sigma), and then stained using Cytofix/cytoperm in accordance with the manufacturer's protocol (BD Bioscience). All samples were analyzed with LSR Fortessa (BD Biosciences) and FlowJo software (Tree Star, St, Ashland, Oreg., USA).

Preparation Example 7: In Vivo Antibody Labeling

The mice were treated with PBS or 1 μg of IL-7-mFc intranasally. To analyze the pulmonary residency of T cells, at 7 and 14 days after IL-7-mFc treatment, 2.5 μg of anti-mouse CD3e-percp-cy5.5 (BD bioscience) was intravenously administered to the mice at 10 min prior to sacrifice (Anderson K G et al., 2014, *Nature protocols* 9:209-222). Residual antibody was removed by cardiac perfusion with PBS, and the lung resident T cell populations in single cell suspensions of lung homogenate were analyzed by flow cytometry.

Preparation Example 8: Histological Analysis and Inflammation Score Measurement

Mice were anesthetized, and the lungs were obtained via thoracotomy and transcardial perfusion with cold PBS. Perfused lungs were immediately fixed with 4% paraformaldehyde, kept at 4° C. overnight, and embedded into paraffin. Lung sections were then stained with hematoxylin and eosin solution (H&E, Sigma Aldrich). The images of whole lung tissues were captured with a Pannoramic MIDI slide scanner (3DHISTECH, Hungary). Pulmonary inflammation was assessed by the degree of peribronchiolar and perivascular inflammation (Choi J P et al., 2010, *Allergy* 65:1322-1330).

Preparation Example 9: mRNA Preparation, cDNA Synthesis, and Quantitative PCR Analysis of Lung Homogenate After preparation of lung homogenate, mRNAs were prepared with a Reliaprep™ mRNA preparation kit (Promega, Fitchburg, Wis., USA), and cDNAs were synthesized with GoScript™ Reverse Transcriptase System (Promega) according to the manufacturer's protocol. Quantitative PCR assay was performed using Power SYBR Green Master Mix (Applied Biosystems, Foster City, Calif.). The following primers for qPCR analysis were synthesized by Genotech (Korea): NS-1 forward, TGCGGGAAAGCAGATAGTGG (SEQ ID NO: 41); NS-1 reverse, TCAGTTAGGTAGCGCGAAGC (SEQ ID NO: 42); L32 forward, GAAACTGGCGGAAACCCA (SEQ ID NO: 43); L32 reverse, and GGATCTGGCCCTTGAACCTT (SEQ ID NO: 44). Relative expression levels of H5N2 NS-1 mRNA were normalized to the level of L32 mRNA.

Preparation Example 10: Statistical Analysis Method

A two-tailed Student's t-test (*, $p<0.05$; , $p<0.01$) was used to evaluate the differences between two groups. A one-way ANOVA with Bonferroni's post-test (, $p<0.01$) was used for more than three groups. Differences in survival rates between groups were determined by a log-rank test (†, $p<0.05$; ††, $p<0.01$).

Example 1: Confirmation of Protective Effect of IL-7 Against IAV Infection and Pathway Dependence BALB/c mice (n=8/group) were treated with 1 µg of IL-7-mFc via various routes such as intranasal (i.n.), intramuscular (i.m.), intraperitoneal (i.p.) and subcutaneous (s.c.) routes, and then infected with 3 $LD_{50}$ of mouse adaptive avian influenza (H5N2, A/Aquatic bird/Korea/ma81/2005) after 2 weeks of IL-7-mFc treatment. The results are shown in FIGS. 1*a* and 1*b*.

Figure 1B:
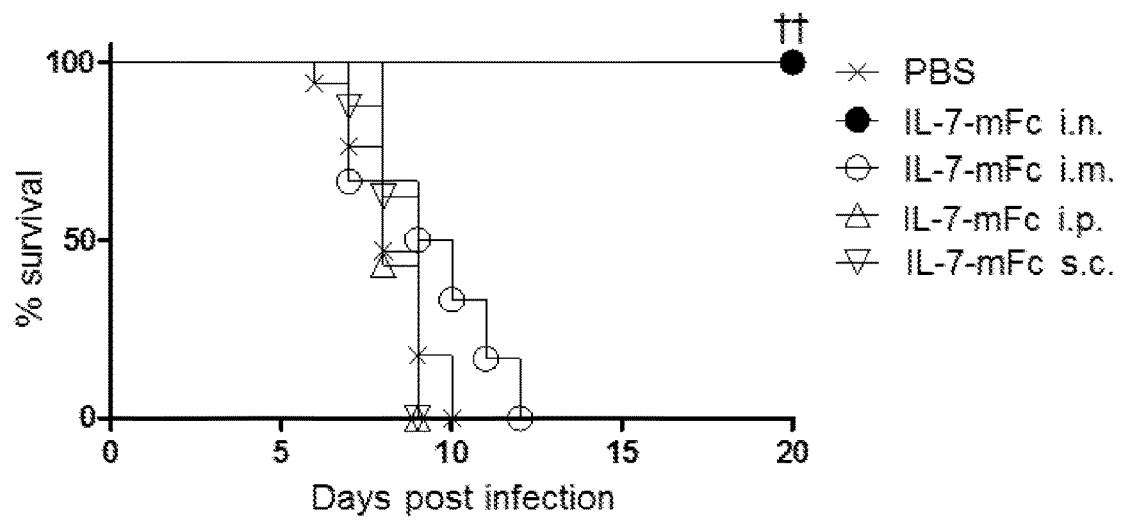

As shown in FIGS. 1*a* and 1*b*, intranasal IL-7-mFc treatment completely protected mice against lethal influenza infection, whereas IL-7-mFc treatment via an intramuscular, intraperitoneal and subcutaneous route showed no significant protection. These results reveal that induction of local immune responses by IL-7-mFc at the pathogen entry site, namely, the airway mucosa, may be critical for the protection against lethal IAV infection.

Example 2: Confirmation of Effective Dosage of IL-7-mFc Against IAV Infection and Function of Fc Fusion of IL-7

BALB/c mice (n=6/group) were treated with various ranges of doses among 0.04 µg to 10 µg of IL-7-mFc and 1 µg to 10 µg of recombinant human IL-7 (rhIL-7), and after 14 days, the mice were infected with 3 $LD_{50}$ of H5N2.

Figure 2A:
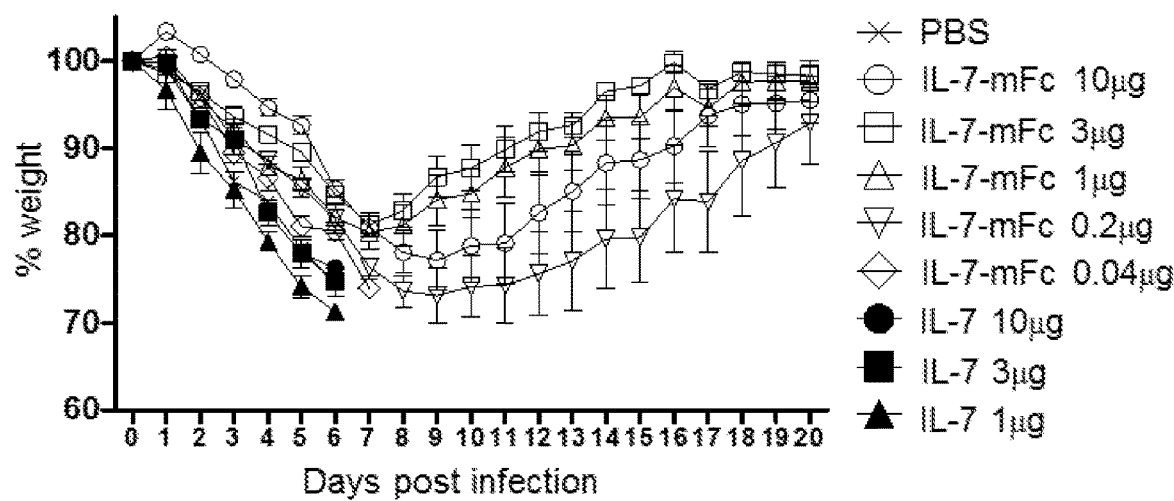
FIGS. 2a and 2b are graphs respectively showing weight change rate with respect to their initial body weight and survival rate of BALB/c mice depending on time passage after intranasal administration of IL-7-mFc and IL-7, respectively, with various doses.
Figure 2B:
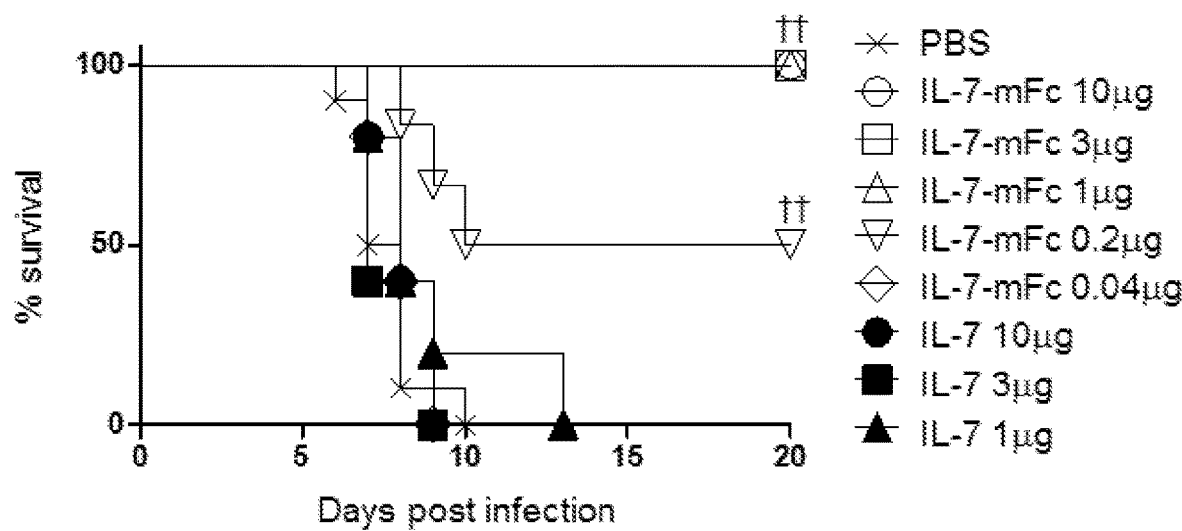

As a result, as shown in FIGS. 2*a* and 2*b*, no protection against IAV infection was observed in the mice treated with 0.04 µg of IL-7-mFc. In the mice treated with 0.2 µg of IL-7-mFc, 50% survival rate and partial protection against IAV were observed. In the mice treated with 1 µg, 3 µg, and 10 µg, i.e., 1 µg or more of IL-7-mFc dose, 100% survival rate and complete protection against IAV were observed. On the other hand, no protection against IAV was observed when 1 µg or more of rhIL-7 without Fc fusion was administered (1 µg, 3 µg and 10 µg).

In addition, BALB/c mice (n=6-8/group) were respectively treated with 1 µg of IL-7-mFc and 1 µg of Fc fragment (for comparison), at 14 days before IAV infection. After infection with 3 $LD_{50}$ of H5N2, the weight change with respect to the initial body weight and survival rate of the mice were observed for 20 days.

Figure 2C:
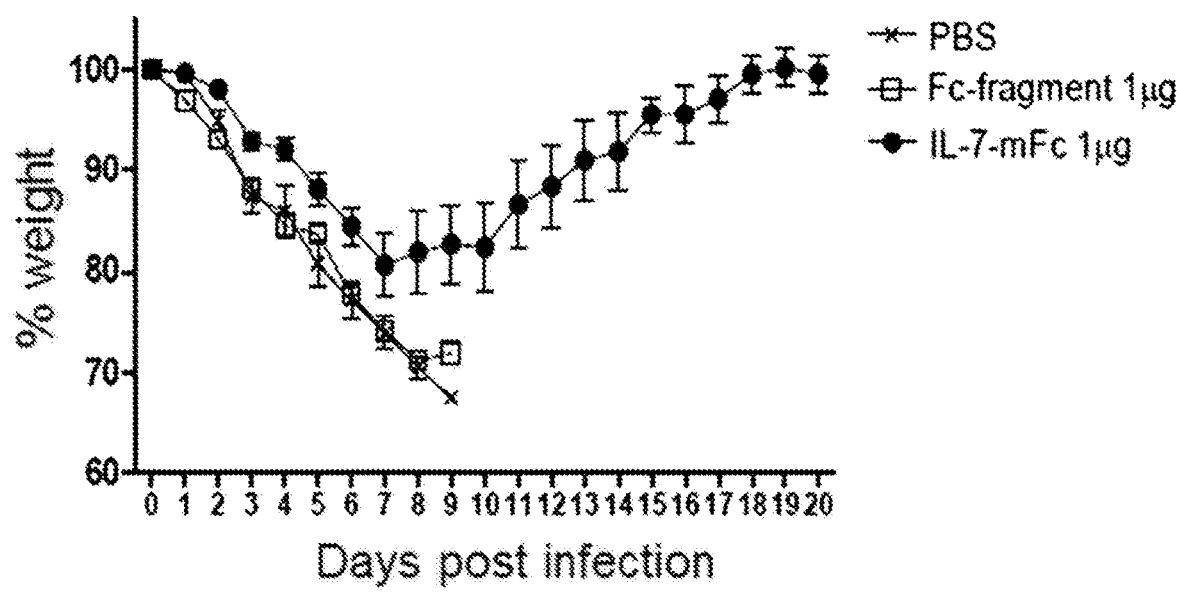
FIGS. 2c and 2d are graphs respectively showing weight change rate with respect to their initial body weight and survival rate of BALB/c mice depending on time passage after administration of 1 µg of IL-7-mFc and Fc-fragment, respectively.
Figure 2D:
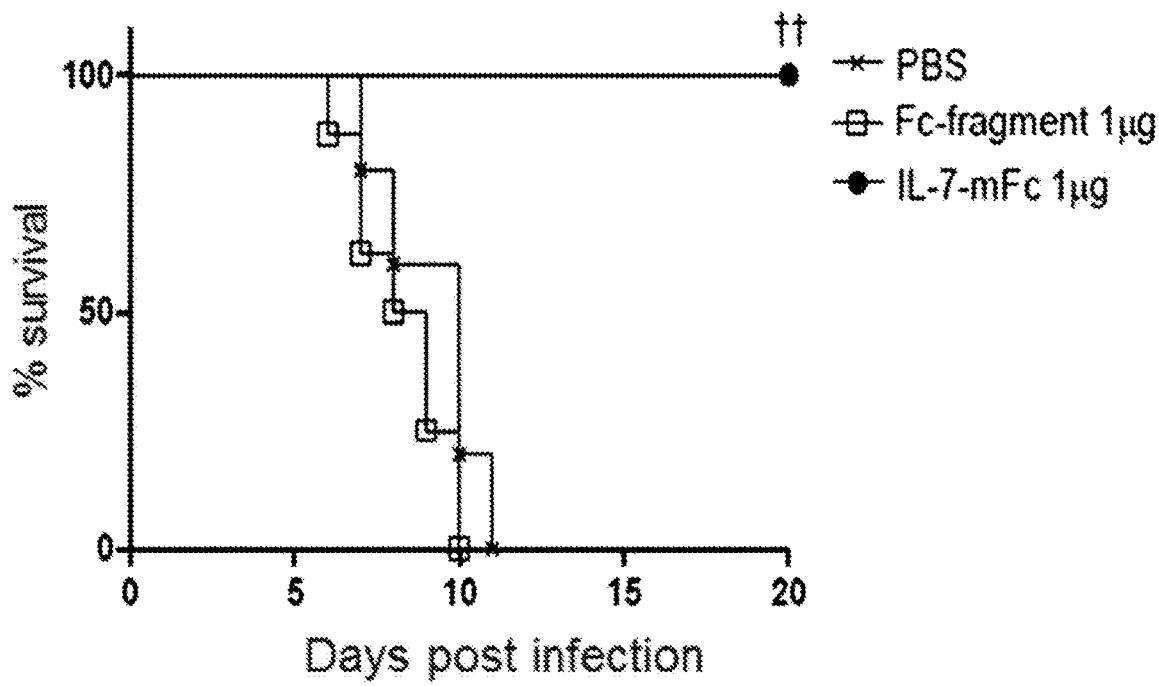

As a result, as shown in FIGS. 2*c* and 2*d*, 100% survival rate was observed in the mice treated with 1 µg of IL-7-mFc, whereas no protection was observed in the mice treated with 1 µg of Fc fragment.

These results confirm that the effective dose of IL-7-mFc for complete protection from IAV infection in mice is 1 µg or more. It was also found that Fc fragment alone did not have protection function against IAV infection.

Example 3: Confirmation of the Relationship Between FcRn and the Protective Effect Against IAV Infection PBS and 1 g of IL-7-mFc, were intranasally administered to C57BL/6 and FcRn$^{-/-}$ (neonatal Fc receptor-deficient) mice (n=8/group), and after 14 days, mice were infected with 3 $LD_{50}$ of H5N2 viruses.

Figure 3A:
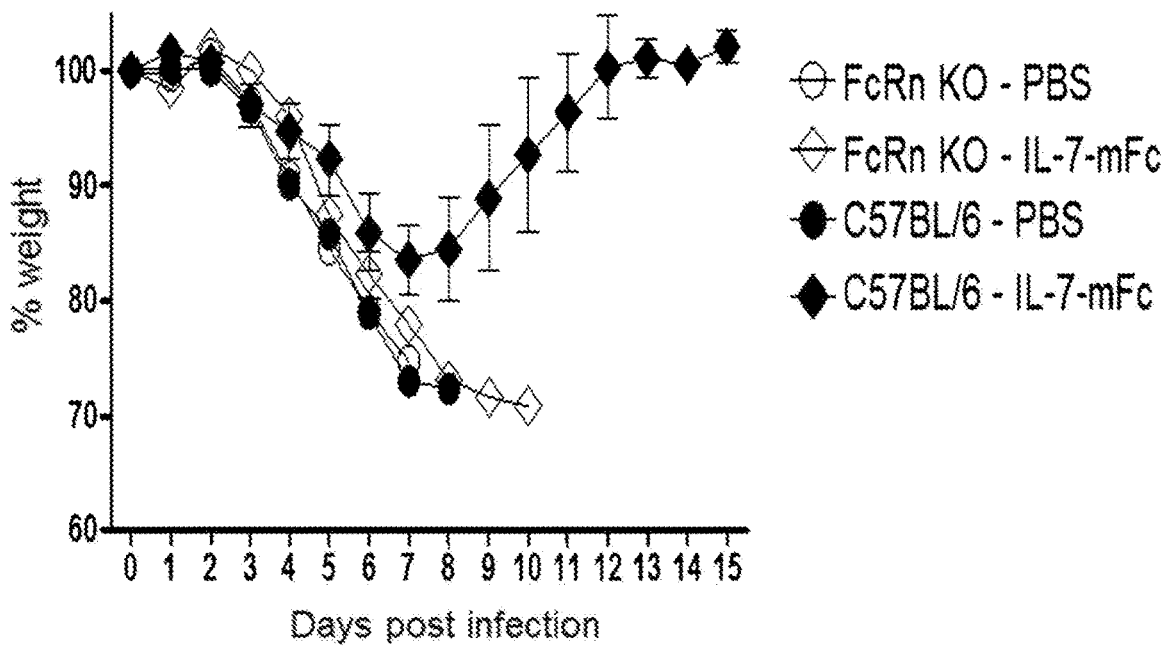
FIGS. 3a and 3b are graphs respectively showing weight change rate with respect to their initial body weight and survival rate of C57BL/6 and FcRn$^{-/-}$ mice depending on time passage after administration of PBS and 1 µg of IL-7-mFc, respectively.
Figure 3B:
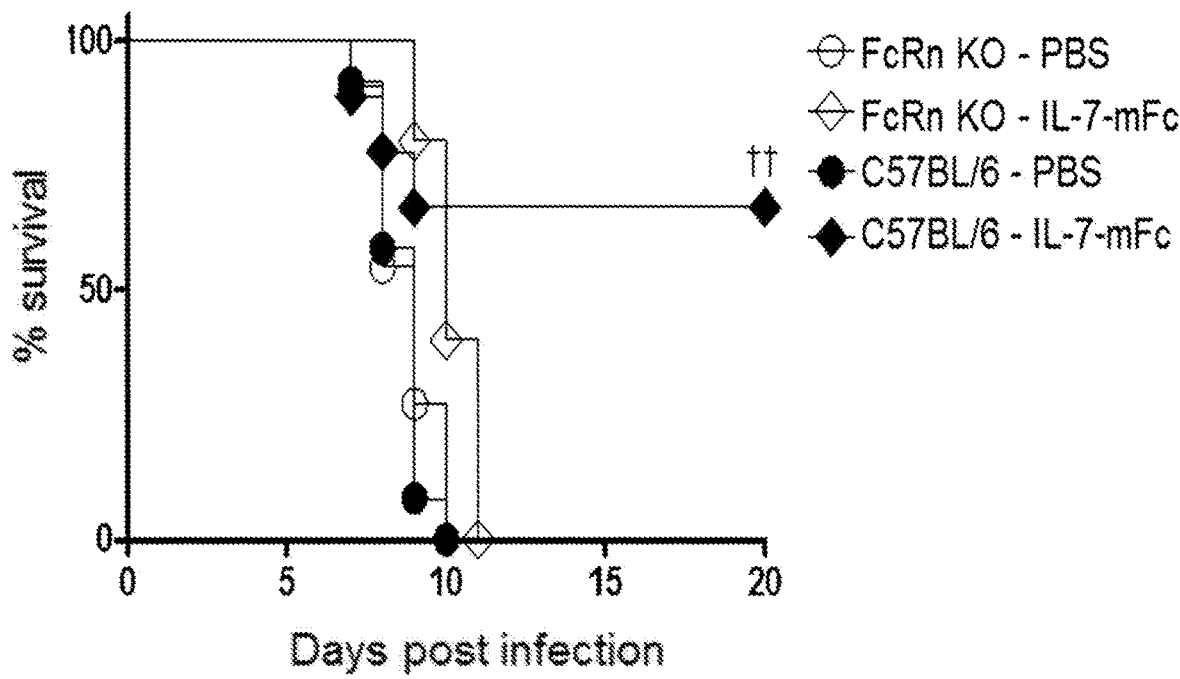

As a result, as shown in FIGS. 3*a* and 3*b*, none of the PBS-administered C57BL/6 and FcRn$^{-/-}$ mice showed any protection against IAV infection. Among the IL-7-mFc-treated mice, C57BL/6 mice showed protection against infection, whereas no protection against IAV infection was observed in FcRn$^{-/-}$ mice.

These results indicate that the protective immune response of the IL-7-Fc fusion protein arised from FcRn-dependent mechanism (transcytosis).

Example 4: Confirmation of Long-Term Protection Effect of IL-7-Fc Fusion Protein Against Lethal IAV Infections BALB/c mice (n=11/group) were infected with 3 $LD_{50}$ of H5N2 at 0, 3, 7, 14, 21 or 35 days after intranasal administration of 1 µg of IL-7-mFc.

Figure 4A:
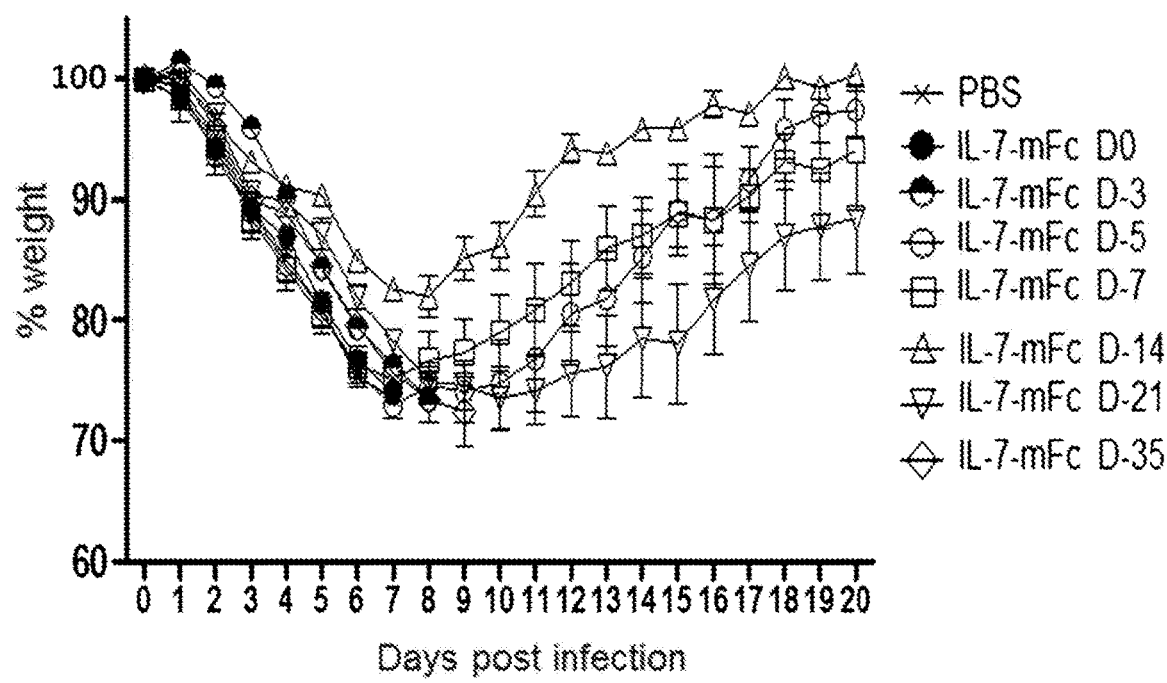
FIGS. 4a and 4b are graphs respectively showing weight change rate with respect to their initial body weight and survival rate of BALB/c mice depending on time passage at day 0, 3, 5, 7, 14, 21 or 35 after intranasal administration of 1 µg of IL-7-mFc.
Figure 4B:
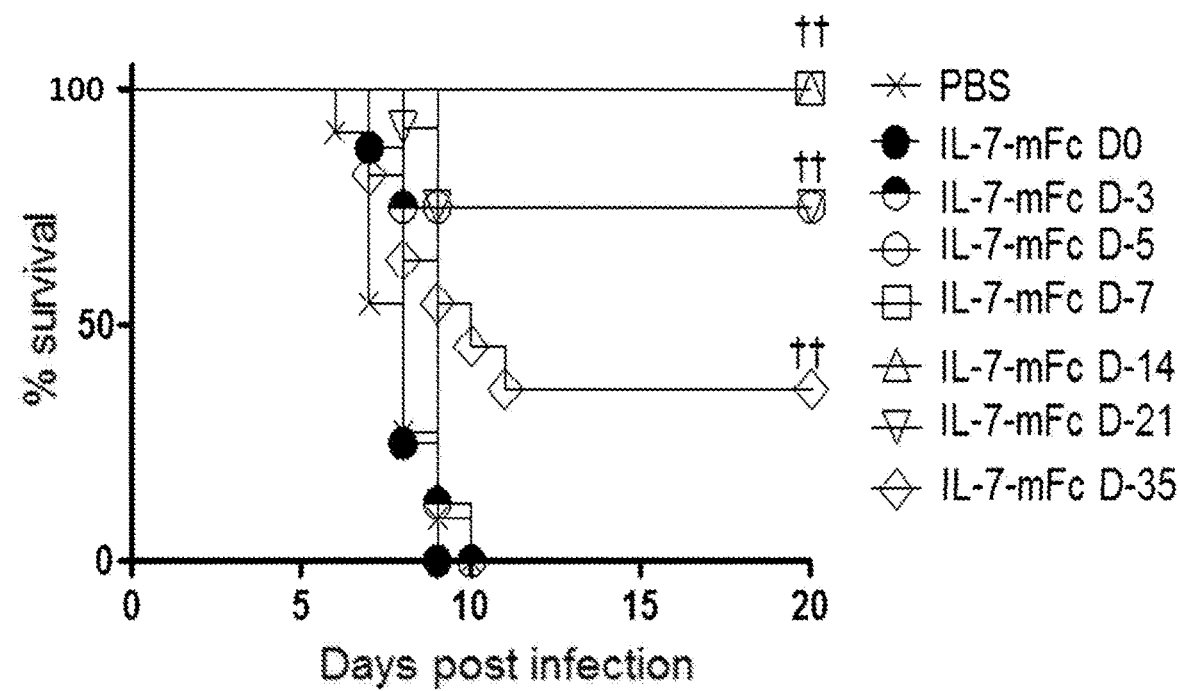
Figure 5A:
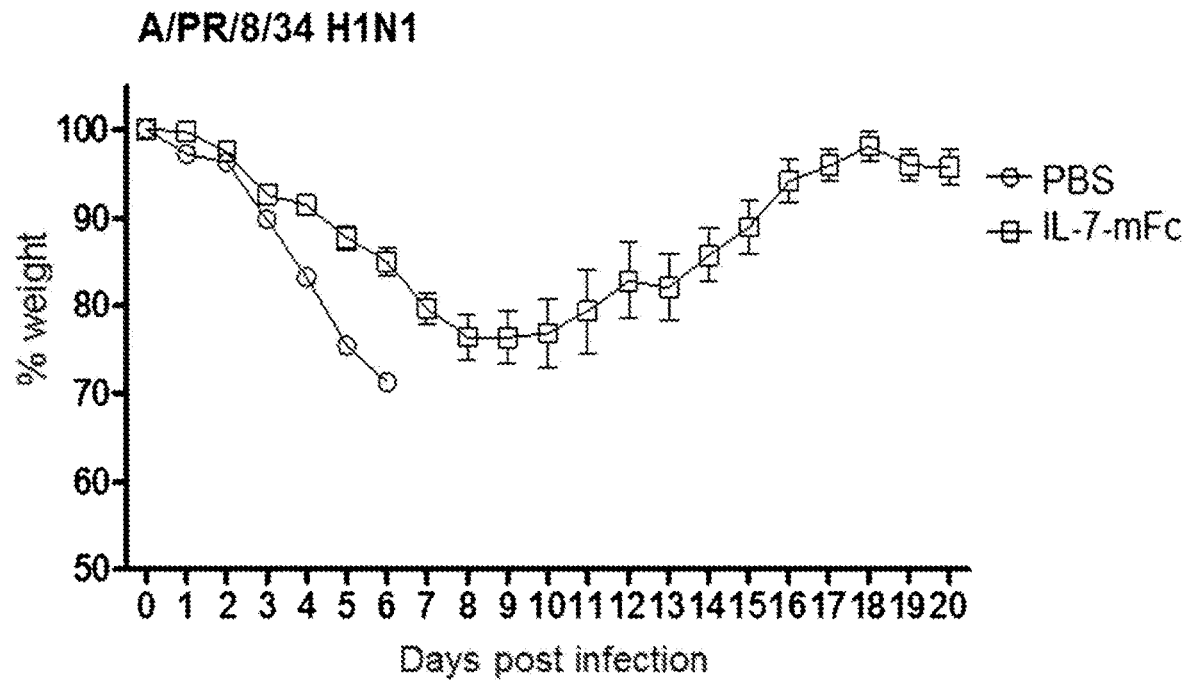
FIGS. 5a to 5f are graphs showing weight change rate with respect to their initial body weight and survival rate of BALB/c mice depending on time passage after infection with a lethal dose of A/PR/8/34 H1N1, A/California/04/09 H1N1 or A/Philippines/2/82 H3N2 at 14 days post-intranasal administration of IL-7-mFc.
Figure 5B:
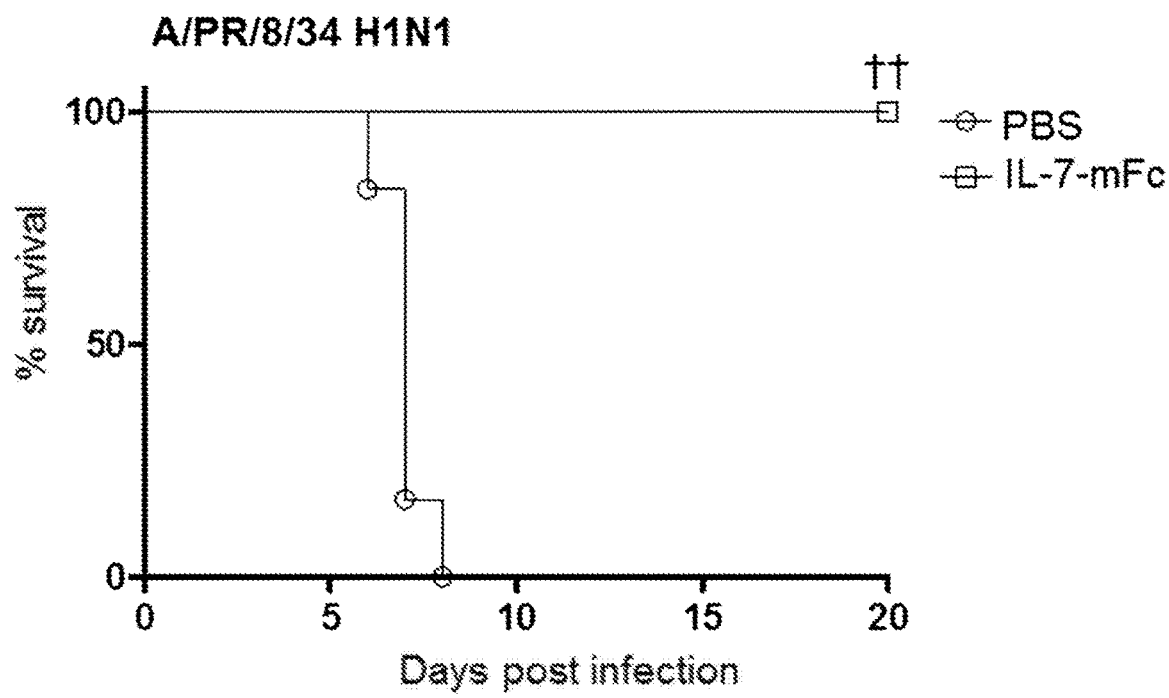
Figure 5C:
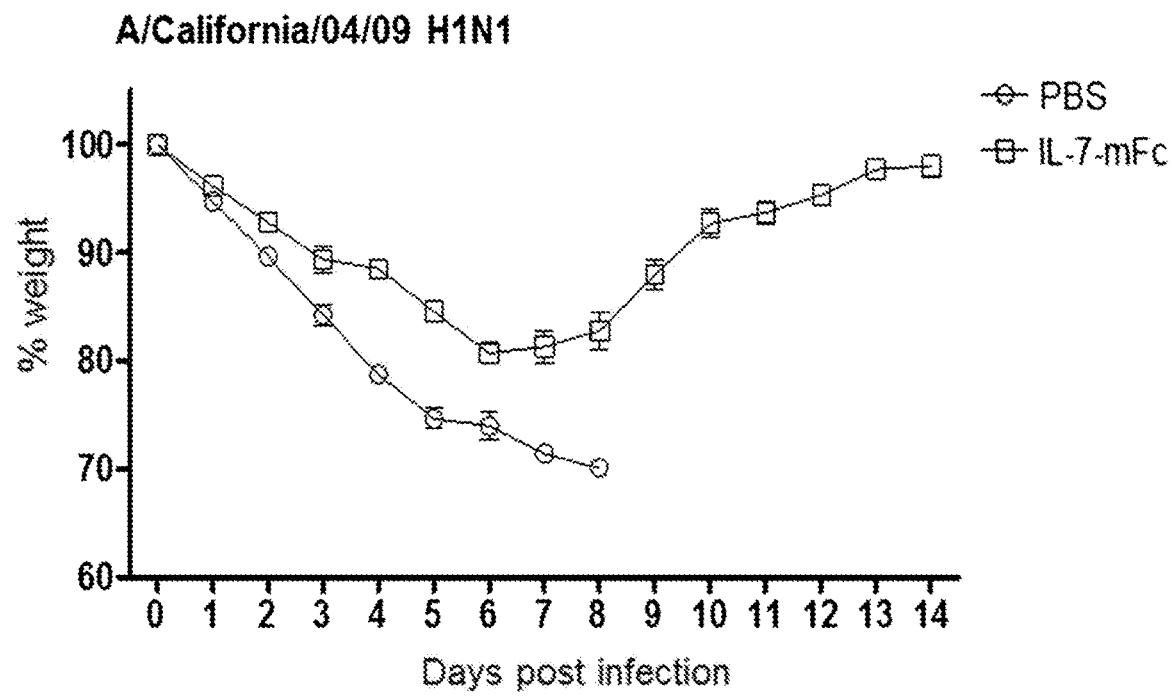
Figure 5D:
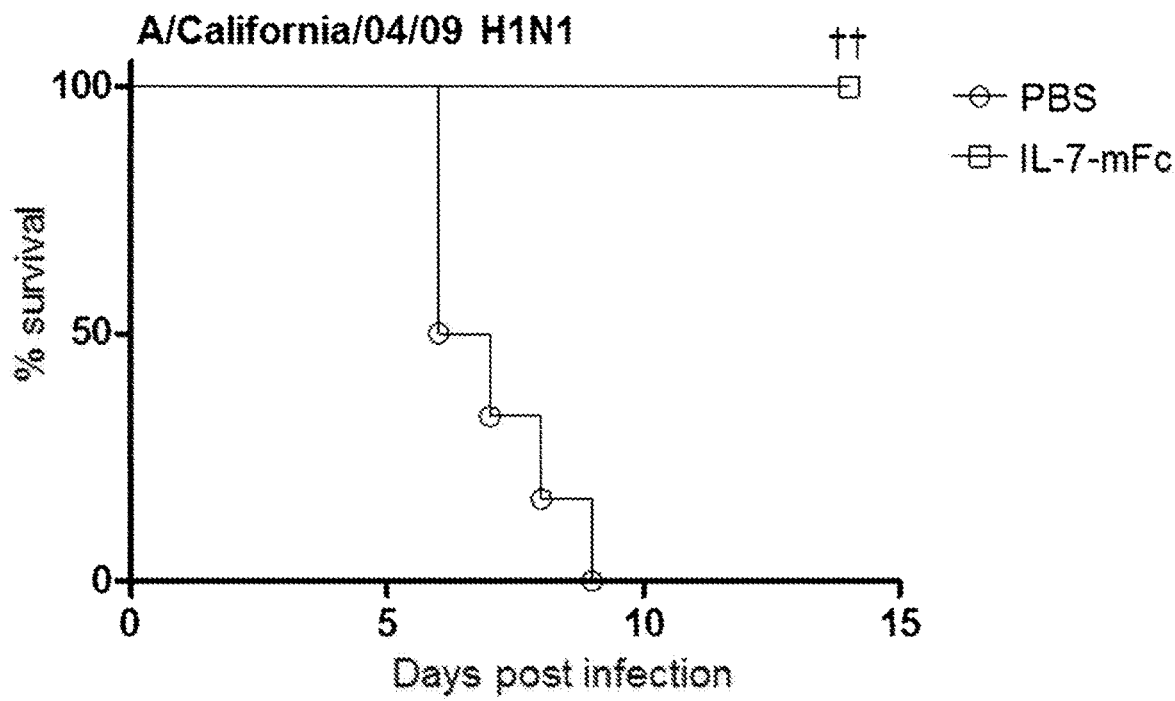
Figure 5E:
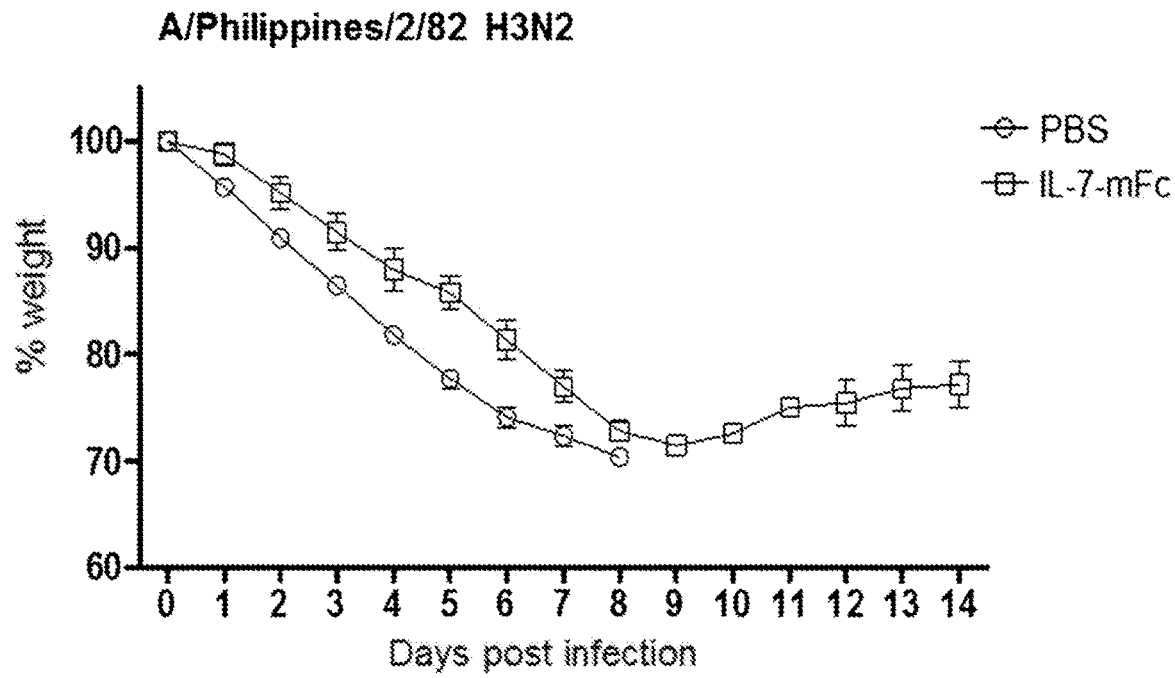
Figure 5F:
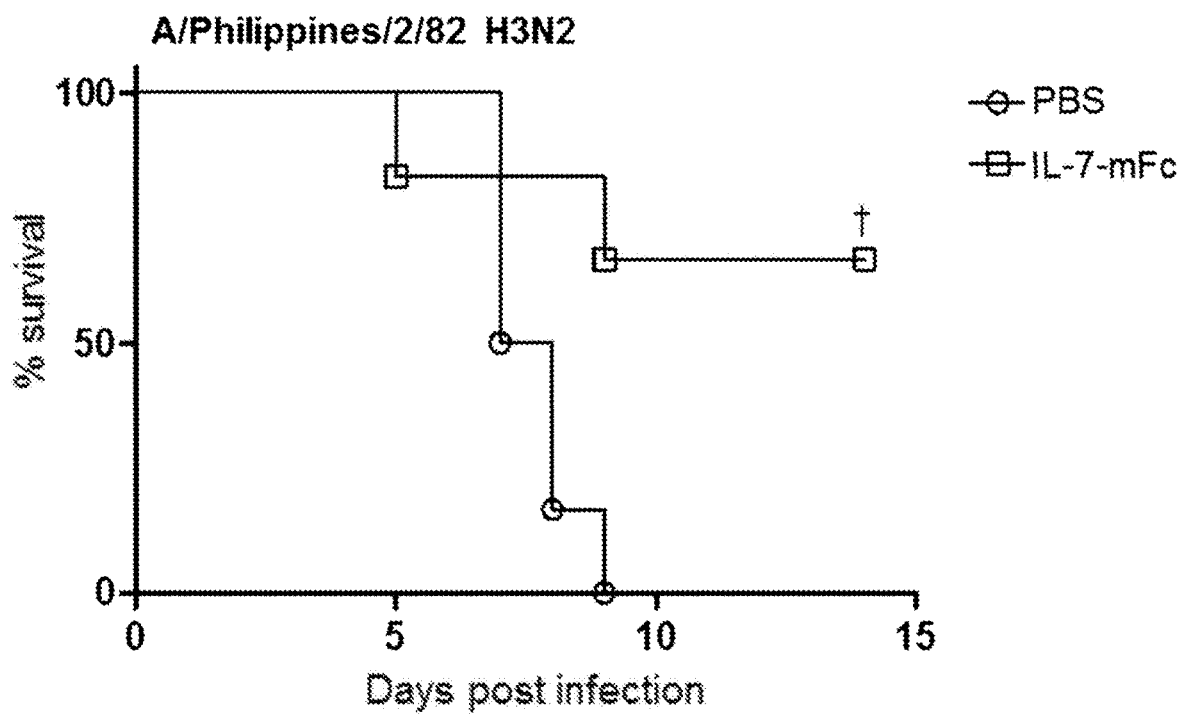

As a result, as shown in FIGS. 4*a* and 4*b*, the protective effect of IL-7-mFc was observed at 5 days after IL-7-mFc treatment, but no protective effect was observed at days 0 to 3. Complete protection against IAV was observed at 7 days and even at 14 days after IL-7-mFc treatment. This protective effect diminished over time but 63% and 36% of mice survival rate were found at 21 days and 35 days after IL-7-mFc treatment, respectively.

These results indicate that the protective effect of IL-7-mFc against IAV infection persists from 5 to 35 days after IL-7-mFc treatment.

Example 5: Confirmation of the Protective Effect of the IL-7-Fc Fusion Protein Against the Variant Virus BALB/c mice (n=6/group) were infected with lethal doses of IAV varians of H1N1 (A/Puerto Rico/8/34 and A/California/04/09) and H3N2 (A/Philippines/2/82) at 14 days after IL-7-mFc nasal administration. The mean weight loss was shown as the percentage relative to the initial weight at the time of infection (mean±SEM) and the survival rate was analyzed by the Kaplan-Meier method. The protective effects of IL-7-mFc against infection of H1N1 (A/Puerto Rico/8/34), H1N1 (A/California/04/09) and H3N2 (A/Philippines/2/82) are shown in FIGS. 5a to 5f.

As shown in FIGS. 5a to 5f, all mice pretreated with IL-7-mFc at 14 days before infection with H1N1 (A/Puerto Rico/8/34), H1N1 (A/California/04/09) and H3N2 (A/Philippines/2/82) showed protective effect.

These results indicate that IL-7-Fc fusion protein effectively induces local immune response regardless of the mutation of the virus, thereby improving the survival rate.

Example 6: Evaluation of Effect of IL-7-Fc Fusion Protein on Pulmonary T Cells

The numbers of lymphocytes in the lung tissues were analyzed at 0, 3, 7, 14, 21, and 35 days after intranasal administration of 1 µg of IL-7-mFc to the mice. At each point, the absolute numbers of immune cells in the total lung homogenate were calculated based on the percentage of the total cells by flow cytometry. The results shown in Table 1 were expressed as the mean±SEM of four mice/group (N.D., not determined; *, $p<0.05$; **, $p<0.01$ by Student's t test compared with cell numbers on day 0 (Table 1)). The expression of CD11a and CD49d in lung CD4 and CD8 T cells of BALBb/c (n=4) mice with $CD62L^{high}CD44^{low}$ and $CD62L^{low}CD44^{high}$ phenotypes to which IL-7-mFc had been administered was analyzed by flow cytometry.

those not labeled (in vivo $CD3^-$ in vitro $CD3^+$) by in vivo CD3 label were analyzed. Through such method, it can be determined that the cells not labeled by in vivo CD3 label are lung retentive cells, and the cells labeled by in vivo CD3 label are those mainly in the bloodstream.

Figure 6:
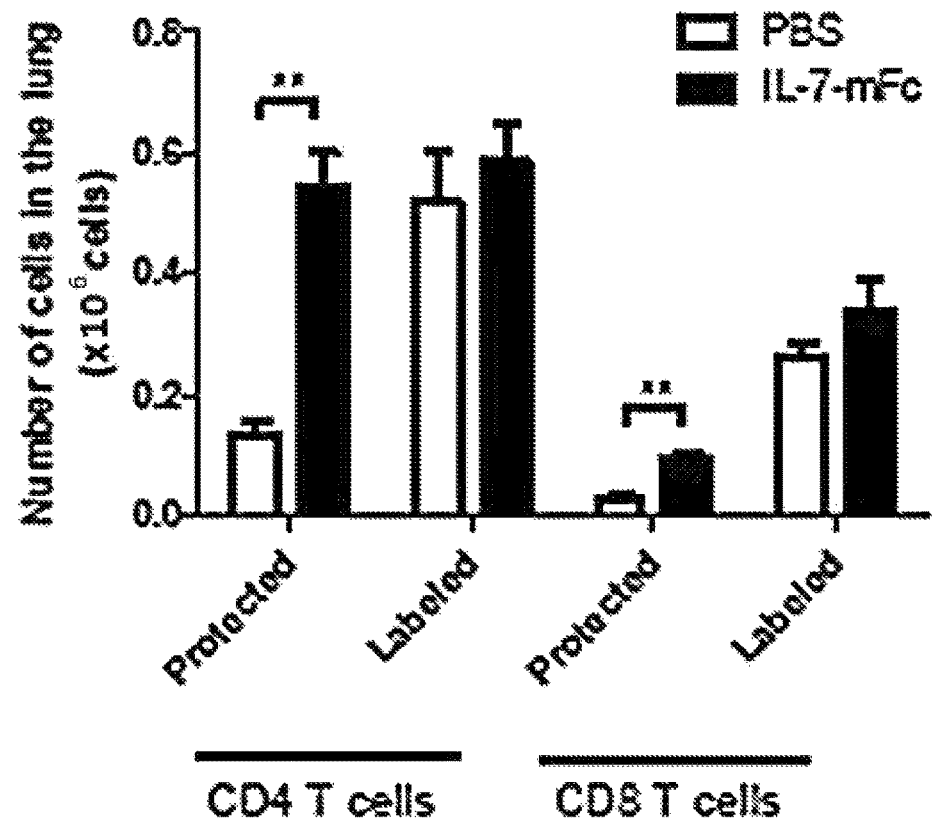
FIG. 6 is a graph showing analysis of $T_{RM}$-like T cells not exposed to the anti-CD3 antibody present in the blood stream but reside in the local tissues, by an in vivo labeling experiment for analyzing the histological location of pulmonary-derived T cells increased by IL-7-mFc treatment.

As shown in FIG. 6, the number of 'labeled' T cells returned to basal levels while the number of 'unlabelled' T cells was still significantly increased even at 14 days after treatment.

Example 8: Effect of Intranasal IL-7-Fc Fusion Protein Pretreatment on the Pulmonary T Cells and H5N2-Specific IgG Titer in the BALF after IAV Infection BALB/c mice were treated with IL-7-mFc intranasally and infected with 3 $LD_{50}$ of H5N2 after 14 days. Absolute numbers of T cells from total lung homogenate were measured at days 3 and 7 after infection. Frequency of $CD62L^{low}CD44^{high}$ population of CD8 and CD4 T cells were analyzed at day 7 after infection. Absolute number of pulmonary B and NK cells were measured at days 3 and 7 after infection. H5N2-specific IgG titer was analyzed in the BALF and sera at day 7 after infection. The results are shown in FIGS. 7a and 7b.

Figure 7A:
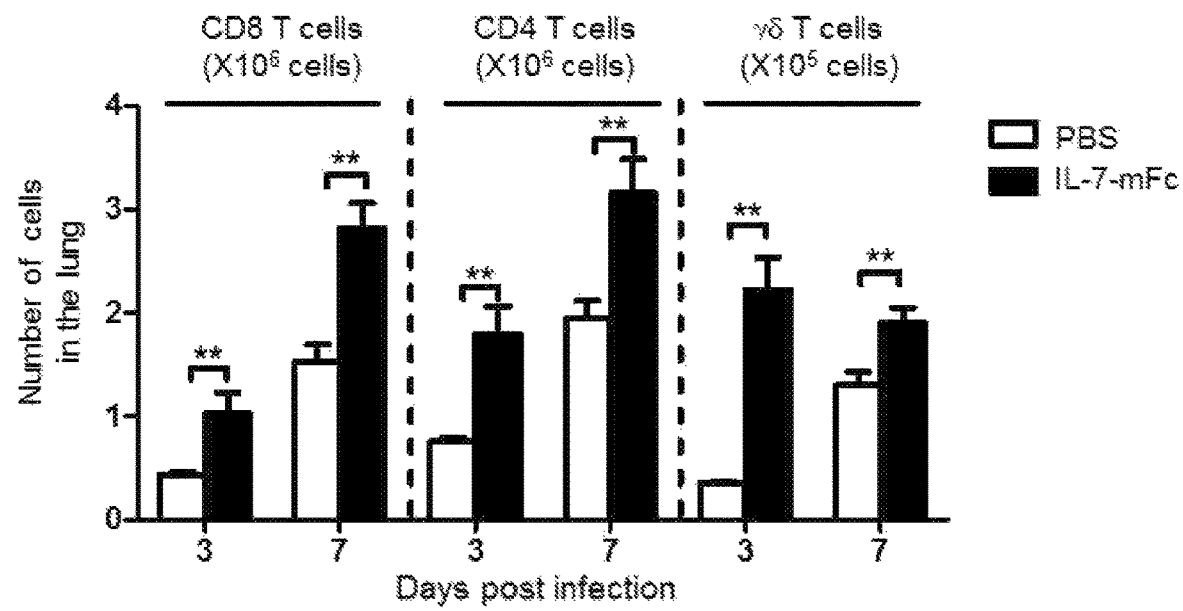
FIGS. 7a and 7b are graphs showing that activated T cells specifically increase and no change of antibody response is observed in the IL-7-mFc pre-administration group after the IAV infection.
Figure 7B:
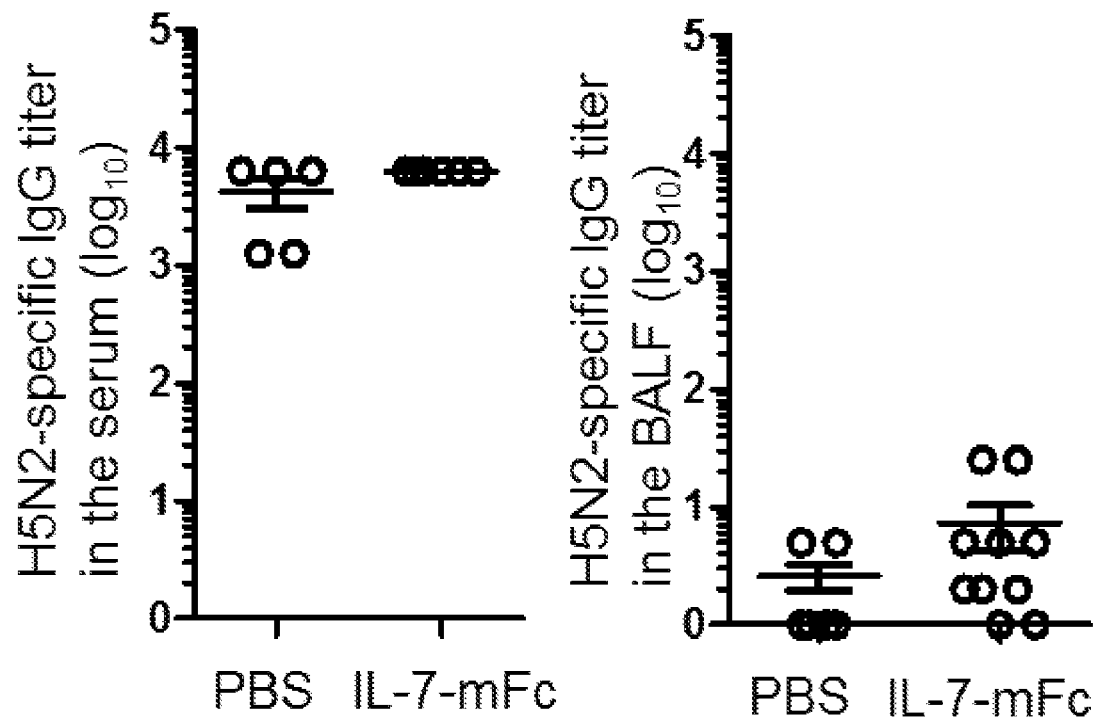

As shown in FIGS. 7a and 7b, the number of pulmonary T cells containing CD8, CD4 and γδ T cells was increased by IL-7-mFc pretreatment after IAV infection compared with PBS treatment, and IAV-specific IgG production in BALF and serum was not further up-regulated.

TABLE 1

| | Absolute cell numbers after IL-7-mFc treatment | | | | | |
|---|---|---|---|---|---|---|
| | Day 0 | Day 3 | Day 7 | Day 14 | Day 21 | Day 35 |
| Total CD4 T cells (×10⁶) | 0.68 ± 0.07 | 0.76 ± 0.03 | 2.08 ± 0.28** | 0.89 ± 0.19 | 0.79 ± 0.14 | 0.70 ± 0.07 |
| $CD62L^{low}CD44^{high}$ CD4 T cells (×10⁵) | 0.58 ± 0.08 | 1.44 ± 0.08** | 7.80 ± 1.24** | 1.61 ± 0.25** | 0.93 ± 0.05** | 0.69 ± 0.05 |
| Total CD8 T cells (×10⁶) | 0.31 ± 0.07 | 0.32 ± 0.01 | 0.75 ± 0.11** | 0.42 ± 0.08 | 0.36 ± 0.08 | 0.28 ± 0.03 |
| $CD62L^{low}CD44^{high}$ CD8 T cells (×10⁵) | 0.18 ± 0.03 | 0.29 ± 0.02* | 1.22 ± 0.14** | 0.50 ± 0.12* | 0.25 ± 0.03 | 0.26 ± 0.04 |
| γδ T cells (×10⁵) | 0.24 ± 0.02 | 0.39 ± 0.01** | 4.71 ± 0.59** | 0.54 ± 0.16** | 0.40 ± 0.06* | 0.38 ± 0.02** |
| B cells (×10⁶) | 0.84 ± 0.17 | 0.97 ± 0.03 | 2.27 ± 0.38* | 1.13 ± 0.10 | 0.83 ± 0.18 | N.D. |
| NK cells (×10⁶) | 0.36 ± 0.03 | 0.58 ± 0.03* | 0.71 ± 0.07** | 0.39 ± 0.04 | 0.29 ± 0.05 | N.D. |

As shown in Table 1, IL-7-mFc significantly and temporarily increased the number of various immune cells including CD127 (receptor of IL-7)-expressing immune cells including CD4, CD8, γδ T cells and B cells.

Example 7: In Vivo Antibody Labelling Experiment to Confirm that Pulmonary T Cells are Lung-Retentive BALB/c mice were sacrificed at 7 days after intranasal administration of PBS and IL-7-mFc. 10 minutes prior to sacrifice, 2.5 µg of CD3 mAb-conjugated Percp-Cy5.5 was administered intravenously to the mice. The remaining antibodies in the blood stream were removed by perfusion and a single cell suspension was prepared. T cells in the bloodstream (circulating T cell) are labeled by antibodies, but T cells in lung tissue (lung-retentive T cells) are not labeled by antibodies. At 7 and 14 days after IL-7-mFc treatment, the numbers of cells labeled (in vivo $CD3^+$ in vitro $CD3^+$) or These results indicate that the IL-7-Fc fusion protein induces a protective effect against fatal IAV infection by significantly increasing T cells directly involved in the immune response rather than the antibody response.

Example 9: Confirmation of the Relationship Between IL-7-Primed T Cells and Virus Removal The viral titer and relative expression of H5N2 NS-1 mRNA (normalized by housekeeping-gene L32) in total lung homogenate were analyzed at day 3 and 7 after infection. The results are shown in FIG. 8.

Figure 8:
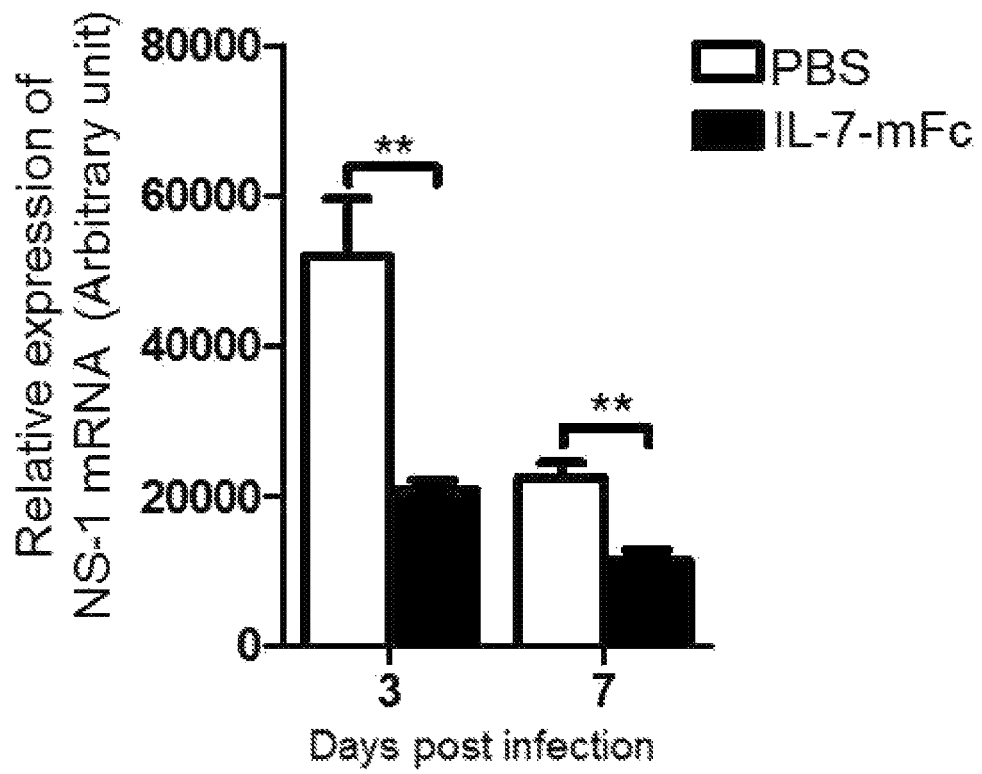
FIG. 8 is a graph showing the reduction of viral genes present in lung tissue of the IL-7-mFc pre-administration group after the IAV infection.

As shown in FIG. 8, the expression level of H5N2 NS-1 mRNA was greatly reduced in the total lung homogenate of IL-7-mFc-treated mice.

Example 10: Effect of IL-7-Fc Fusion Protein on Pulmonary Pathology Induced by IAV Infection BALB/c mice were treated with intranasal administration of IL-7-mFc, and after 14 days, infected with 3 $LD_{50}$ of H5N2. H & E staining and total inflammation index of lung sections at 50× magnification, and total protein concentration in BALF were analyzed at day 7 after infection.

Figure 9A:
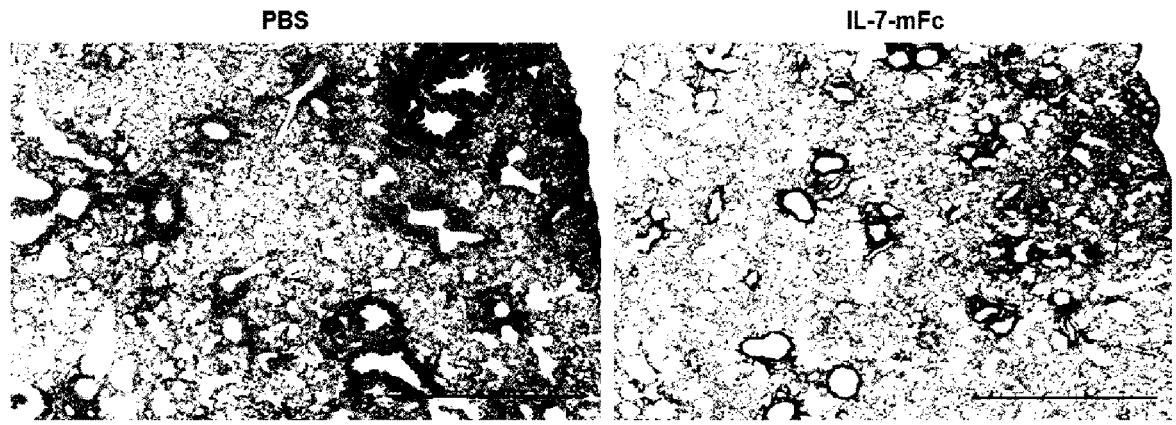
FIGS. 9a and 9b are graphs showing lung tissue lesions and the reducing effect of inflammatory cells in the IL-7-mFc pre-administration group after the IAV infection.
Figure 9B:
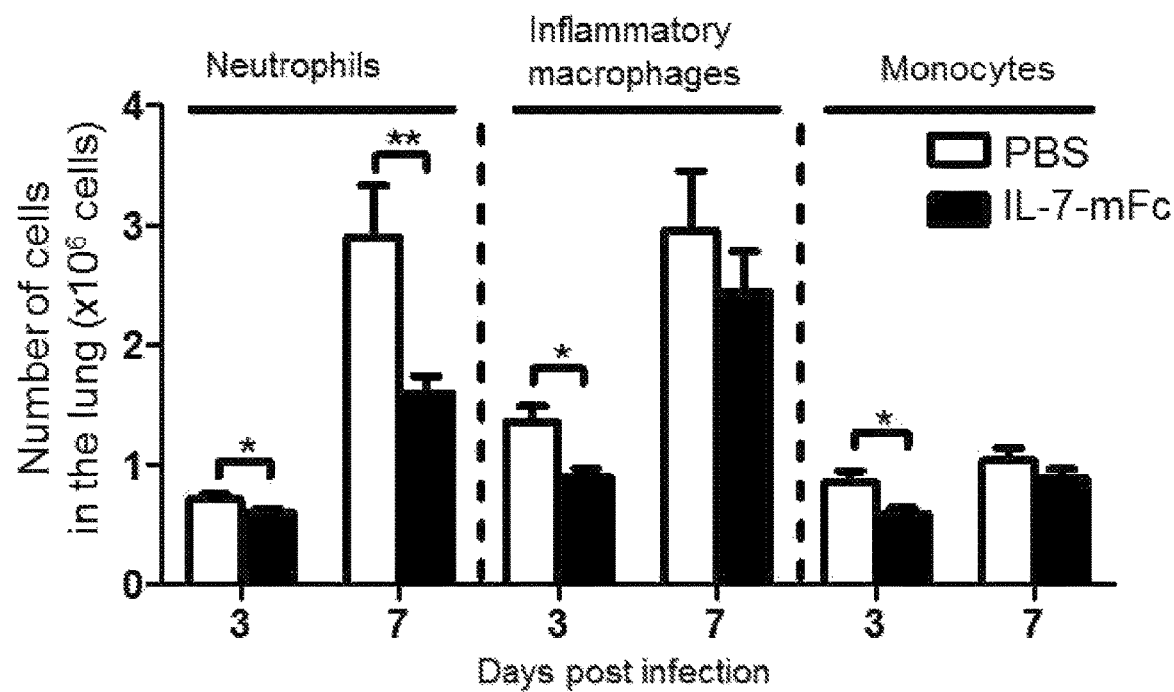

As shown in FIGS. 9a and 9b, the histopathological parameters for airway inflammation after 7 days post-infection was significantly reduced in the lungs of mice given IL-7-mFc pretreatment compared to PBS-treated mice (FIG. 9a). The number of pulmonary neutrophils (Gr-1$^{high}$Ly6c$^{low}$CD11b$^+$) was sharply decreased in IL-7-mFc-treated mice at days 3 and 7 after infection, and the numbers of monocytes (CD11b$^+$CD11c$^-$Ly6c$^+$) and inflammatory macrophages (CD11b$^+$CD11c$^+$MHCII$^+$Ly6c$^+$F4/80$^+$) were also decreased at day 3 after infection in IL-7-mFc-treated mice (FIG. 9b).

The invention claimed is:

1. A method for preventing or treating a disease caused by influenza virus in a subject in need thereof, comprising administering to the subject an effective amount of a composition comprising an interleukin-7 (IL-7) fusion protein and a pharmaceutically acceptable carrier, wherein the administration is an intranasal administration; and wherein the IL-7 fusion protein is represented by the formula:

N'-Fc-A-IL-7-C' or N'-A-IL-7-Fc-C' wherein

N' is the N-terminus of the fusion protein;

C' is the C-terminus of the fusion protein;

A is selected from the group consisting of glycine, methionine-methionine, glycine-glycine, methionine-glycine, glycine-methionine, methionine-methionine-methionine, methionine-methionine-glycine, methionine-glycine-methionine, glycine-methionine-methionine, methionine-glycine-glycine, glycine-methionine-glycine, glycine-glycine- methionine, and glycine-glycine-glycine;

IL-7 is an interleukin 7 comprising the amino acid sequence of SEQ ID NO: 1, 2, 3, 4, 5, or 6; and Fc comprises the amino acid sequence of SEQ ID NO: 9, 10, 11, 12, 13, or 14.

2. The method of claim 1, wherein the A-IL-7 of the formula:

N'-Fc-A-IL-7-C' or N'-A-IL-7-Fc-C' comprises the amino acid sequence of SEQ ID NO: 15, 16, 17, 18, 19 or 20.

3. The method of claim 1, wherein the IL-7 is fused directly to the N-terminus or C-terminus of the immunoglobulin Fc region or fused via a linker.

4. The method of claim 1, wherein in the formula N'-A-IL-7-Fc-C', the A-IL-7 is linked directly to the N-terminus of the immunoglobulin Fc region or via a linker.

5. The method of claim 1, wherein the influenza virus is H7N9, H5N1, H5N2, H3N2 or H1N1.

6. A method of reducing an expression of influenza virus mRNA in a subject in need thereof comprising administering to the subject an effective amount of a composition comprising an interleukin-7 (IL-7) fusion protein, and a pharmaceutically acceptable carrier, wherein the administration is an intranasal administration; and wherein the IL-7 fusion protein is represented by the formula:

N'-Fc-A-IL-7-C' or N'-A-IL-7-Fc-C' wherein

N' is the N-terminus of the fusion protein;

C' is the C-terminus of the fusion protein;

A is selected from the group consisting of glycine, methionine-methionine, glycine-glycine, methionine-glycine, glycine-methionine, methionine-methionine-methionine, methionine-methionine-glycine, methionine-glycine-methionine, glycine-methionine-methionine, methionine-glycine-glycine, glycine-methionine-glycine, glycine-glycine-methionine, and glycine-glycine-glycine;

IL-7 is an interleukin 7 comprising the amino acid sequence of SEQ ID NO: 1, 2, 3, 4, 5 or 6; and Fc comprises the amino acid sequence of SEQ ID NO: 9, 10, 11, 12, 13, or 14.

7. A method of protecting a subject from influenza virus infection comprising administering to the subject a composition comprising an interleukin-7 (IL-7) fusion protein, and a pharmaceutically acceptable carrier, wherein the administering is carried out by an intranasal route; and wherein the IL-7 fusion protein is represented by the formula:

N'-Fc-A-IL-7-C' or N'-A-IL-7-Fc-C' wherein

N' is the N-terminus of the fusion protein;

C' is the C-terminus of the fusion protein;

A is selected from the group consisting of glycine, methionine-methionine, glycine-glycine, methionine-glycine, glycine-methionine, methionine-methionine-methionine, methionine-methionine-glycine, methionine-glycine-methionine, glycine-methionine-methionine, methionine-glycine-glycine, glycine-methionine-glycine, glycine-glycine-methionine, and glycine-glycine-glycine;

IL-7 is an interleukin 7 comprising the amino acid sequence of SEQ ID NO: 1, 2, 3, 4, 5 or 6; and Fc comprises the amino acid sequence of SEQ ID NO: 9, 10, 11, 12, 13, or 14.

8. A method for preventing or treating a disease caused by influenza virus in a subject in need thereof, comprising administering to the subject an effective amount of a composition comprising an interleukin-7 (IL-7) fusion protein and a pharmaceutically acceptable carrier via an intranasal administration,
wherein the IL-7 fusion protein comprises the amino acid sequence of SEQ ID NO: 22, 23, 24, or 25.

* * * * *

SEQUENCE LISTING

```
<160> NUMBER OF SEQ ID NOS: 44

<210> SEQ ID NO 1
<211> LENGTH: 177
<212> TYPE: PRT
<213> ORGANISM: Artificial Sequence
<220> FEATURE:
<223> OTHER INFORMATION: amino acid sequence of human IL-7 (Accession
      number : P13232)

<400> SEQUENCE: 1

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
    50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His

<210> SEQ ID NO 2
<211> LENGTH: 154
<212> TYPE: PRT
<213> ORGANISM: Artificial Sequence
<220> FEATURE:
<223> OTHER INFORMATION: amino acid sequence of rat IL-7 (Accession
      number : P56478)

<400> SEQUENCE: 2

Met Phe His Val Ser Phe Arg Tyr Ile Phe Gly Ile Pro Pro Leu Ile
1               5                   10                  15

Leu Val Leu Leu Pro Val Thr Ser Ser Asp Cys His Ile Lys Asp Lys
            20                  25                  30

Asp Gly Lys Ala Phe Gly Ser Val Leu Met Ile Ser Ile Asn Gln Leu
        35                  40                  45

Asp Lys Met Thr Gly Thr Asp Ser Asp Cys Pro Asn Asn Glu Pro Asn
```

-continued

```
                    50                  55                  60
Phe Phe Lys Lys His Leu Cys Asp Asp Thr Lys Glu Ala Ala Phe Leu
 65                  70                  75                  80

Asn Arg Ala Ala Arg Lys Leu Arg Gln Phe Leu Lys Met Asn Ile Ser
                 85                  90                  95

Glu Glu Phe Asn Asp His Leu Leu Arg Val Ser Asp Gly Thr Gln Thr
            100                 105                 110

Leu Val Asn Cys Thr Ser Lys Glu Glu Lys Thr Ile Lys Glu Gln Lys
        115                 120                 125

Lys Asn Asp Pro Cys Phe Leu Lys Arg Leu Leu Arg Glu Ile Lys Thr
    130                 135                 140

Cys Trp Asn Lys Ile Leu Lys Gly Ser Ile
145                 150
```

<210> SEQ ID NO 3
<211> LENGTH: 154
<212> TYPE: PRT
<213> ORGANISM: Artificial Sequence
<220> FEATURE:
<223> OTHER INFORMATION: amino acid sequence of mouse IL-7 (Accession
      number : P10168)

<400> SEQUENCE: 3

```
Met Phe His Val Ser Phe Arg Tyr Ile Phe Gly Ile Pro Pro Leu Ile
 1               5                  10                  15

Leu Val Leu Leu Pro Val Thr Ser Ser Glu Cys His Ile Lys Asp Lys
                20                  25                  30

Glu Gly Lys Ala Tyr Glu Ser Val Leu Met Ile Ser Ile Asp Glu Leu
            35                  40                  45

Asp Lys Met Thr Gly Thr Asp Ser Asn Cys Pro Asn Asn Glu Pro Asn
        50                  55                  60

Phe Phe Arg Lys His Val Cys Asp Asp Thr Lys Glu Ala Ala Phe Leu
 65                  70                  75                  80

Asn Arg Ala Ala Arg Lys Leu Lys Gln Phe Leu Lys Met Asn Ile Ser
                 85                  90                  95

Glu Glu Phe Asn Val His Leu Leu Thr Val Ser Gln Gly Thr Gln Thr
            100                 105                 110

Leu Val Asn Cys Thr Ser Lys Glu Glu Lys Asn Val Lys Glu Gln Lys
        115                 120                 125

Lys Asn Asp Ala Cys Phe Leu Lys Arg Leu Leu Arg Glu Ile Lys Thr
    130                 135                 140

Cys Trp Asn Lys Ile Leu Lys Gly Ser Ile
145                 150
```

<210> SEQ ID NO 4
<211> LENGTH: 177
<212> TYPE: PRT
<213> ORGANISM: Artificial Sequence
<220> FEATURE:
<223> OTHER INFORMATION: amino acid sequence of monkey IL-7 (Accession
      number : NP_001279008)

<400> SEQUENCE: 4

```
Met Phe His Val Ser Phe Arg Tyr Ile Phe Gly Leu Pro Pro Leu Ile
 1               5                  10                  15

Leu Val Leu Leu Pro Val Ala Ser Ser Asp Cys Asp Ile Glu Gly Lys
                20                  25                  30

Asp Gly Lys Gln Tyr Glu Ser Val Leu Met Val Ser Ile Asp Gln Leu
```

```
                35                  40                  45

Leu Asp Ser Met Lys Glu Ile Gly Ser Asn Cys Leu Asn Asn Glu Phe
 50                  55                  60

Asn Phe Phe Lys Arg His Leu Cys Asp Asp Asn Lys Glu Gly Met Phe
 65                  70                  75                  80

Leu Phe Arg Ala Ala Arg Lys Leu Lys Gln Phe Leu Lys Met Asn Ser
                 85                  90                  95

Thr Gly Asp Phe Asp Leu His Leu Leu Lys Val Ser Glu Gly Thr Thr
                100                 105                 110

Ile Leu Leu Asn Cys Thr Gly Lys Val Lys Gly Arg Lys Pro Ala Ala
                115                 120                 125

Leu Gly Glu Pro Gln Pro Thr Lys Ser Leu Glu Glu Asn Lys Ser Leu
130                 135                 140

Lys Glu Gln Lys Lys Leu Asn Asp Ser Cys Phe Leu Lys Arg Leu Leu
145                 150                 155                 160

Gln Lys Ile Lys Thr Cys Trp Asn Lys Ile Leu Met Gly Thr Lys Glu
                165                 170                 175

His

<210> SEQ ID NO 5
<211> LENGTH: 176
<212> TYPE: PRT
<213> ORGANISM: Artificial Sequence
<220> FEATURE:
<223> OTHER INFORMATION: amino acid sequence of cow IL-7 (Accession
      number : P26895)

<400> SEQUENCE: 5

Met Phe His Val Ser Phe Arg Tyr Ile Phe Gly Ile Pro Pro Leu Ile
 1               5                  10                  15

Leu Val Leu Leu Pro Val Ala Ser Ser Asp Cys Asp Ile Ser Gly Lys
                 20                  25                  30

Asp Gly Gly Ala Tyr Gln Asn Val Leu Met Val Asn Ile Asp Asp Leu
                 35                  40                  45

Asp Asn Met Ile Asn Phe Asp Ser Asn Cys Leu Asn Asn Glu Pro Asn
 50                  55                  60

Phe Phe Lys Lys His Ser Cys Asp Asp Asn Lys Glu Ala Ser Phe Leu
 65                  70                  75                  80

Asn Arg Ala Ser Arg Lys Leu Arg Gln Phe Leu Lys Met Asn Ile Ser
                 85                  90                  95

Asp Asp Phe Lys Leu His Leu Ser Thr Val Ser Gln Gly Thr Leu Thr
                100                 105                 110

Leu Leu Asn Cys Thr Ser Lys Gly Lys Gly Arg Lys Pro Pro Ser Leu
                115                 120                 125

Ser Glu Ala Gln Pro Thr Lys Asn Leu Glu Glu Asn Lys Ser Ser Lys
130                 135                 140

Glu Gln Lys Lys Gln Asn Asp Leu Cys Phe Leu Lys Ile Leu Leu Gln
145                 150                 155                 160

Lys Ile Lys Thr Cys Trp Asn Lys Ile Leu Arg Gly Ile Lys Glu His
                165                 170                 175

<210> SEQ ID NO 6
<211> LENGTH: 176
<212> TYPE: PRT
<213> ORGANISM: Artificial Sequence
<220> FEATURE:
<223> OTHER INFORMATION: amino acid sequence of sheep IL-7 (Accession
``` number : Q28540)

<400> SEQUENCE: 6

Met Phe His Val Ser Phe Arg Tyr Ile Phe Gly Ile Pro Pro Leu Ile
1               5                   10                  15

Leu Val Leu Leu Pro Val Ala Ser Ser Asp Cys Asp Phe Ser Gly Lys
                20                  25                  30

Asp Gly Gly Ala Tyr Gln Asn Val Leu Met Val Ser Ile Asp Asp Leu
            35                  40                  45

Asp Asn Met Ile Asn Phe Asp Ser Asn Cys Leu Asn Asn Glu Pro Asn
        50                  55                  60

Phe Phe Lys Lys His Ser Cys Asp Asp Asn Lys Glu Ala Ser Phe Leu
65                  70                  75                  80

Asn Arg Ala Ala Arg Lys Leu Lys Gln Phe Leu Lys Met Asn Ile Ser
                85                  90                  95

Asp Asp Phe Lys Leu His Leu Ser Thr Val Ser Gln Gly Thr Leu Thr
            100                 105                 110

Leu Leu Asn Cys Thr Ser Lys Gly Lys Gly Arg Lys Pro Pro Ser Leu
        115                 120                 125

Gly Glu Ala Gln Pro Thr Lys Asn Leu Glu Glu Asn Lys Ser Leu Lys
    130                 135                 140

Glu Gln Arg Lys Gln Asn Asp Leu Cys Phe Leu Lys Ile Leu Leu Gln
145                 150                 155                 160

Lys Ile Lys Thr Cys Trp Asn Lys Ile Leu Arg Gly Ile Thr Glu His
                165                 170                 175

<210> SEQ ID NO 7
<211> LENGTH: 384
<212> TYPE: PRT
<213> ORGANISM: Artificial Sequence
<220> FEATURE:
<223> OTHER INFORMATION: amino acid sequence of human IgD constant
      region (Genbank accession No. P01880)

<400> SEQUENCE: 7

Ala Pro Thr Lys Ala Pro Asp Val Phe Pro Ile Ile Ser Gly Cys Arg
1               5                   10                  15

His Pro Lys Asp Asn Ser Pro Val Val Leu Ala Cys Leu Ile Thr Gly
                20                  25                  30

Tyr His Pro Thr Ser Val Thr Val Thr Trp Tyr Met Gly Thr Gln Ser
            35                  40                  45

Gln Pro Gln Arg Thr Phe Pro Glu Ile Gln Arg Arg Asp Ser Tyr Tyr
        50                  55                  60

Met Thr Ser Ser Gln Leu Ser Thr Pro Leu Gln Gln Trp Arg Gln Gly
65                  70                  75                  80

Glu Tyr Lys Cys Val Val Gln His Thr Ala Ser Lys Ser Lys Lys Glu
                85                  90                  95

Ile Phe Arg Trp Pro Glu Ser Pro Lys Ala Gln Ala Ser Ser Val Pro
            100                 105                 110

Thr Ala Gln Pro Gln Ala Glu Gly Ser Leu Ala Lys Ala Thr Thr Ala
        115                 120                 125

Pro Ala Thr Thr Arg Asn Thr Gly Arg Gly Gly Glu Glu Lys Lys Lys
    130                 135                 140

Glu Lys Glu Lys Glu Glu Gln Glu Glu Arg Glu Thr Lys Thr Pro Glu
145                 150                 155                 160

Cys Pro Ser His Thr Gln Pro Leu Gly Val Tyr Leu Leu Thr Pro Ala

```
                165                 170                 175
Val Gln Asp Leu Trp Leu Arg Asp Lys Ala Thr Phe Thr Cys Phe Val
            180                 185                 190

Val Gly Ser Asp Leu Lys Asp Ala His Leu Thr Trp Glu Val Ala Gly
            195                 200                 205

Lys Val Pro Thr Gly Gly Val Glu Glu Gly Leu Leu Glu Arg His Ser
            210                 215                 220

Asn Gly Ser Gln Ser Gln His Ser Arg Leu Thr Leu Pro Arg Ser Leu
225                 230                 235                 240

Trp Asn Ala Gly Thr Ser Val Thr Cys Thr Leu Asn His Pro Ser Leu
            245                 250                 255

Pro Pro Gln Arg Leu Met Ala Leu Arg Glu Pro Ala Ala Gln Ala Pro
            260                 265                 270

Val Lys Leu Ser Leu Asn Leu Leu Ala Ser Ser Asp Pro Pro Glu Ala
            275                 280                 285

Ala Ser Trp Leu Leu Cys Glu Val Ser Gly Phe Ser Pro Pro Asn Ile
            290                 295                 300

Leu Leu Met Trp Leu Glu Asp Gln Arg Glu Val Asn Thr Ser Gly Phe
305                 310                 315                 320

Ala Pro Ala Arg Pro Pro Gln Pro Gly Ser Thr Thr Phe Trp Ala
                325                 330                 335

Trp Ser Val Leu Arg Val Pro Ala Pro Ser Pro Gln Pro Ala Thr
            340                 345                 350

Tyr Thr Cys Val Val Ser His Glu Asp Ser Arg Thr Leu Leu Asn Ala
            355                 360                 365

Ser Arg Ser Leu Glu Val Ser Tyr Val Thr Asp His Gly Pro Met Lys
            370                 375                 380

<210> SEQ ID NO 8
<211> LENGTH: 327
<212> TYPE: PRT
<213> ORGANISM: Artificial Sequence
<220> FEATURE:
<223> OTHER INFORMATION: amino acid sequence of Partial human IgG4
      constant region (Genbank accession No. AAH25985)

<400> SEQUENCE: 8

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
            85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140
```

```
Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 9
<211> LENGTH: 245
<212> TYPE: PRT
<213> ORGANISM: Artificial Sequence
<220> FEATURE:
<223> OTHER INFORMATION: amino acid sequence of hFc01

<400> SEQUENCE: 9

Arg Asn Thr Gly Arg Gly Gly Glu Glu Lys Lys Lys Glu Lys Glu Lys
1               5                   10                  15

Glu Glu Gln Glu Glu Arg Glu Thr Lys Thr Pro Glu Cys Pro Ser His
                20                  25                  30

Thr Gln Pro Leu Gly Val Phe Leu Phe Pro Pro Lys Pro Lys Asp Thr
            35                  40                  45

Leu Met Ile Ser Arg Thr Pro Glu Val Thr Cys Val Val Val Asp Val
        50                  55                  60

Ser Gln Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Gly Leu Pro Ser
        115                 120                 125

Ser Ile Glu Lys Thr Ile Ser Lys Ala Lys Gly Gln Pro Arg Glu Pro
    130                 135                 140

Gln Val Tyr Thr Leu Pro Pro Ser Gln Glu Glu Met Thr Lys Asn Gln
145                 150                 155                 160

Val Ser Leu Thr Cys Leu Val Lys Gly Phe Tyr Pro Ser Asp Ile Ala
                165                 170                 175
```

```
Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Arg Leu
            195                 200                 205

Thr Val Asp Lys Ser Arg Trp Gln Glu Gly Asn Val Phe Ser Cys Ser
            210                 215                 220

Val Met His Glu Ala Leu His Asn His Tyr Thr Gln Lys Ser Leu Ser
225                 230                 235                 240

Leu Ser Leu Gly Lys
            245

<210> SEQ ID NO 10
<211> LENGTH: 245
<212> TYPE: PRT
<213> ORGANISM: Artificial Sequence
<220> FEATURE:
<223> OTHER INFORMATION: amino acid sequence of hFc02

<400> SEQUENCE: 10

Arg Asn Thr Gly Arg Gly Gly Glu Glu Lys Lys Gly Gly Lys Glu Lys
1               5                   10                  15

Glu Glu Gln Glu Glu Arg Glu Thr Lys Thr Pro Glu Cys Pro Ser His
            20                  25                  30

Thr Gln Pro Leu Gly Val Phe Leu Phe Pro Pro Lys Pro Lys Asp Thr
            35                  40                  45

Leu Met Ile Ser Arg Thr Pro Glu Val Thr Cys Val Val Val Asp Val
        50                  55                  60

Ser Gln Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Gly Leu Pro Ser
        115                 120                 125

Ser Ile Glu Lys Thr Ile Ser Lys Ala Lys Gly Gln Pro Arg Glu Pro
    130                 135                 140

Gln Val Tyr Thr Leu Pro Pro Ser Gln Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Arg Leu
            195                 200                 205

Thr Val Asp Lys Ser Arg Trp Gln Glu Gly Asn Val Phe Ser Cys Ser
            210                 215                 220

Val Met His Glu Ala Leu His Asn His Tyr Thr Gln Lys Ser Leu Ser
225                 230                 235                 240

Leu Ser Leu Gly Lys
            245

<210> SEQ ID NO 11
<211> LENGTH: 245
<212> TYPE: PRT
<213> ORGANISM: Artificial Sequence
<220> FEATURE:
```

<223> OTHER INFORMATION: amino acid sequence of hFc03

<400> SEQUENCE: 11

Arg Asn Thr Gly Arg Gly Gly Glu Glu Lys Gly Ser Lys Glu Lys
1               5                   10                  15

Glu Glu Gln Glu Glu Arg Glu Thr Lys Thr Pro Glu Cys Pro Ser His
            20                  25                  30

Thr Gln Pro Leu Gly Val Phe Leu Phe Pro Pro Lys Pro Lys Asp Thr
            35                  40                  45

Leu Met Ile Ser Arg Thr Pro Glu Val Thr Cys Val Val Val Asp Val
50                  55                  60

Ser Gln Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Gly Leu Pro Ser
        115                 120                 125

Ser Ile Glu Lys Thr Ile Ser Lys Ala Lys Gly Gln Pro Arg Glu Pro
    130                 135                 140

Gln Val Tyr Thr Leu Pro Pro Ser Gln Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Arg Leu
        195                 200                 205

Thr Val Asp Lys Ser Arg Trp Gln Gln Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Leu Gly Lys
            245

<210> SEQ ID NO 12
<211> LENGTH: 245
<212> TYPE: PRT
<213> ORGANISM: Artificial Sequence
<220> FEATURE:
<223> OTHER INFORMATION: amino acid sequence of hFc04

<400> SEQUENCE: 12

Arg Asn Thr Gly Arg Gly Gly Glu Glu Lys Ser Gly Lys Glu Lys
1               5                   10                  15

Glu Glu Gln Glu Glu Arg Glu Thr Lys Thr Pro Glu Cys Pro Ser His
            20                  25                  30

Thr Gln Pro Leu Gly Val Phe Leu Phe Pro Pro Lys Pro Lys Asp Thr
            35                  40                  45

Leu Met Ile Ser Arg Thr Pro Glu Val Thr Cys Val Val Val Asp Val
50                  55                  60

Ser Gln Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Tyr Arg Val Val Ser Val Leu Thr Val Leu His Gln Asp Trp Leu
                100                 105                 110

Asn Gly Lys Glu Tyr Lys Cys Lys Val Ser Asn Lys Gly Leu Pro Ser
            115                 120                 125

Ser Ile Glu Lys Thr Ile Ser Lys Ala Lys Gly Gln Pro Arg Glu Pro
    130                 135                 140

Gln Val Tyr Thr Leu Pro Pro Ser Gln Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Arg Leu
    195                 200                 205

Thr Val Asp Lys Ser Arg Trp Gln Glu Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Leu Gly Lys
            245

<210> SEQ ID NO 13
<211> LENGTH: 245
<212> TYPE: PRT
<213> ORGANISM: Artificial Sequence
<220> FEATURE:
<223> OTHER INFORMATION: amino acid sequence of hFc05

<400> SEQUENCE: 13

Arg Asn Thr Gly Arg Gly Gly Glu Glu Lys Lys Ser Ser Lys Glu Lys
1               5                   10                  15

Glu Glu Gln Glu Glu Arg Glu Thr Lys Thr Pro Glu Cys Pro Ser His
            20                  25                  30

Thr Gln Pro Leu Gly Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser Gln Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Tyr Arg Val Val Ser Val Leu Thr Val Leu His Gln Asp Trp Leu
                100                 105                 110

Asn Gly Lys Glu Tyr Lys Cys Lys Val Ser Asn Lys Gly Leu Pro Ser
            115                 120                 125

Ser Ile Glu Lys Thr Ile Ser Lys Ala Lys Gly Gln Pro Arg Glu Pro
    130                 135                 140

Gln Val Tyr Thr Leu Pro Pro Ser Gln Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Arg Leu
    195                 200                 205

```
Thr Val Asp Lys Ser Arg Trp Gln Glu Gly Asn Val Phe Ser Cys Ser
            210                 215                 220
Val Met His Glu Ala Leu His Asn His Tyr Thr Gln Lys Ser Leu Ser
225                 230                 235                 240
Leu Ser Leu Gly Lys
            245

<210> SEQ ID NO 14
<211> LENGTH: 243
<212> TYPE: PRT
<213> ORGANISM: Artificial Sequence
<220> FEATURE:
<223> OTHER INFORMATION: amino acid sequence of mouse IgG Fc variant

<400> SEQUENCE: 14

Ala Ser Ala Glu Pro Arg Gly Pro Thr Ile Lys Pro Cys Pro Pro Cys
1               5                   10                  15
Lys Cys Pro Ala Pro Asn Leu Glu Gly Gly Pro Ser Val Phe Ile Phe
            20                  25                  30
Pro Pro Lys Ile Lys Asp Val Leu Met Ile Ser Leu Ser Pro Ile Val
            35                  40                  45
Thr Cys Val Val Val Asp Val Ser Glu Asp Asp Pro Asp Val Gln Ile
        50                  55                  60
Ser Trp Phe Val Asn Asn Val Glu Val His Thr Ala Gln Thr Gln Thr
65                  70                  75                  80
His Arg Glu Asp Tyr Asn Ser Thr Leu Arg Val Val Ser Ala Leu Pro
                85                  90                  95
Ile Gln His Gln Asp Trp Met Ser Gly Lys Ala Phe Ala Cys Ala Val
            100                 105                 110
Asn Asn Lys Asp Leu Pro Ala Pro Ile Glu Arg Thr Ile Ser Lys Pro
            115                 120                 125
Lys Gly Ser Val Arg Ala Pro Gln Val Tyr Val Leu Pro Pro Pro Glu
        130                 135                 140
Glu Glu Met Thr Lys Lys Gln Val Thr Leu Thr Cys Met Val Thr Asp
145                 150                 155                 160
Phe Met Pro Glu Asp Ile Tyr Val Glu Trp Thr Asn Asn Gly Lys Thr
                165                 170                 175
Glu Leu Asn Tyr Lys Asn Thr Glu Pro Val Leu Asp Ser Asp Gly Ser
            180                 185                 190
Tyr Phe Met Tyr Ser Lys Leu Arg Val Glu Lys Lys Asn Trp Val Glu
            195                 200                 205
Arg Asn Ser Tyr Ser Cys Ser Val Val His Glu Gly Leu His Asn His
        210                 215                 220
His Thr Thr Lys Ser Phe Ser Arg Thr Pro Gly Lys Gly Gly Gly Asn
225                 230                 235                 240
Ser Gly Ser

<210> SEQ ID NO 15
<211> LENGTH: 153
<212> TYPE: PRT
<213> ORGANISM: Artificial Sequence
<220> FEATURE:
<223> OTHER INFORMATION: amino acid sequence of modified IL-7(M)

<400> SEQUENCE: 15

Met Asp Cys Asp Ile Glu Gly Lys Asp Gly Lys Gln Tyr Glu Ser Val
1               5                   10                  15
```

Leu Met Val Ser Ile Asp Gln Leu Leu Asp Ser Met Lys Glu Ile Gly
            20                  25                  30

Ser Asn Cys Leu Asn Asn Glu Phe Asn Phe Phe Lys Arg His Ile Cys
        35                  40                  45

Asp Ala Asn Lys Glu Gly Met Phe Leu Phe Arg Ala Ala Arg Lys Leu
    50                  55                  60

Arg Gln Phe Leu Lys Met Asn Ser Thr Gly Asp Phe Asp Leu His Leu
65                  70                  75                  80

Leu Lys Val Ser Glu Gly Thr Thr Ile Leu Leu Asn Cys Thr Gly Gln
                85                  90                  95

Val Lys Gly Arg Lys Pro Ala Ala Leu Gly Glu Ala Gln Pro Thr Lys
            100                 105                 110

Ser Leu Glu Glu Asn Lys Ser Leu Lys Glu Gln Lys Lys Leu Asn Asp
        115                 120                 125

Leu Cys Phe Leu Lys Arg Leu Leu Gln Glu Ile Lys Thr Cys Trp Asn
    130                 135                 140

Lys Ile Leu Met Gly Thr Lys Glu His
145                 150

<210> SEQ ID NO 16
<211> LENGTH: 154
<212> TYPE: PRT
<213> ORGANISM: Artificial Sequence
<220> FEATURE:
<223> OTHER INFORMATION: amino acid sequence of modified IL-7(MM)

<400> SEQUENCE: 16

Met Met Asp Cys Asp Ile Glu Gly Lys Asp Gly Lys Gln Tyr Glu Ser
1               5                   10                  15

Val Leu Met Val Ser Ile Asp Gln Leu Leu Asp Ser Met Lys Glu Ile
            20                  25                  30

Gly Ser Asn Cys Leu Asn Asn Glu Phe Asn Phe Phe Lys Arg His Ile
        35                  40                  45

Cys Asp Ala Asn Lys Glu Gly Met Phe Leu Phe Arg Ala Ala Arg Lys
    50                  55                  60

Leu Arg Gln Phe Leu Lys Met Asn Ser Thr Gly Asp Phe Asp Leu His
65                  70                  75                  80

Leu Leu Lys Val Ser Glu Gly Thr Thr Ile Leu Leu Asn Cys Thr Gly
                85                  90                  95

Gln Val Lys Gly Arg Lys Pro Ala Ala Leu Gly Glu Ala Gln Pro Thr
            100                 105                 110

Lys Ser Leu Glu Glu Asn Lys Ser Leu Lys Glu Gln Lys Lys Leu Asn
        115                 120                 125

Asp Leu Cys Phe Leu Lys Arg Leu Leu Gln Glu Ile Lys Thr Cys Trp
    130                 135                 140

Asn Lys Ile Leu Met Gly Thr Lys Glu His
145                 150

<210> SEQ ID NO 17
<211> LENGTH: 155
<212> TYPE: PRT
<213> ORGANISM: Artificial Sequence
<220> FEATURE:
<223> OTHER INFORMATION: amino acid sequence of modified IL-7(MMM)

<400> SEQUENCE: 17

Met Met Met Asp Cys Asp Ile Glu Gly Lys Asp Gly Lys Gln Tyr Glu

```
    1               5                   10                  15
Ser Val Leu Met Val Ser Ile Asp Gln Leu Leu Asp Ser Met Lys Glu
            20                  25                  30

Ile Gly Ser Asn Cys Leu Asn Asn Glu Phe Asn Phe Lys Arg His
            35                  40                  45

Ile Cys Asp Ala Asn Lys Glu Gly Met Phe Leu Phe Arg Ala Ala Arg
        50                  55                  60

Lys Leu Arg Gln Phe Leu Lys Met Asn Ser Thr Gly Asp Phe Asp Leu
65                  70                  75                  80

His Leu Leu Lys Val Ser Glu Gly Thr Thr Ile Leu Leu Asn Cys Thr
                    85                  90                  95

Gly Gln Val Lys Gly Arg Lys Pro Ala Ala Leu Gly Glu Ala Gln Pro
                100                 105                 110

Thr Lys Ser Leu Glu Glu Asn Lys Ser Leu Lys Glu Gln Lys Lys Leu
                115                 120                 125

Asn Asp Leu Cys Phe Leu Lys Arg Leu Leu Gln Glu Ile Lys Thr Cys
            130                 135                 140

Trp Asn Lys Ile Leu Met Gly Thr Lys Glu His
145                 150                 155

<210> SEQ ID NO 18
<211> LENGTH: 155
<212> TYPE: PRT
<213> ORGANISM: Artificial Sequence
<220> FEATURE:
<223> OTHER INFORMATION: amino acid sequence of modified IL-7(MGM)

<400> SEQUENCE: 18

Met Gly Met Asp Cys Asp Ile Glu Gly Lys Asp Gly Lys Gln Tyr Glu
1               5                   10                  15

Ser Val Leu Met Val Ser Ile Asp Gln Leu Leu Asp Ser Met Lys Glu
            20                  25                  30

Ile Gly Ser Asn Cys Leu Asn Asn Glu Phe Asn Phe Lys Arg His
            35                  40                  45

Ile Cys Asp Ala Asn Lys Glu Gly Met Phe Leu Phe Arg Ala Ala Arg
        50                  55                  60

Lys Leu Arg Gln Phe Leu Lys Met Asn Ser Thr Gly Asp Phe Asp Leu
65                  70                  75                  80

His Leu Leu Lys Val Ser Glu Gly Thr Thr Ile Leu Leu Asn Cys Thr
                    85                  90                  95

Gly Gln Val Lys Gly Arg Lys Pro Ala Ala Leu Gly Glu Ala Gln Pro
                100                 105                 110

Thr Lys Ser Leu Glu Glu Asn Lys Ser Leu Lys Glu Gln Lys Lys Leu
                115                 120                 125

Asn Asp Leu Cys Phe Leu Lys Arg Leu Leu Gln Glu Ile Lys Thr Cys
            130                 135                 140

Trp Asn Lys Ile Leu Met Gly Thr Lys Glu His
145                 150                 155

<210> SEQ ID NO 19
<211> LENGTH: 155
<212> TYPE: PRT
<213> ORGANISM: Artificial Sequence
<220> FEATURE:
<223> OTHER INFORMATION: amino acid sequence of modified IL-7(DDD)

<400> SEQUENCE: 19
```

```
Asp Asp Asp Asp Cys Asp Ile Glu Gly Lys Asp Gly Lys Gln Tyr Glu
1               5                   10                  15
Ser Val Leu Met Val Ser Ile Asp Gln Leu Leu Asp Ser Met Lys Glu
                20                  25                  30
Ile Gly Ser Asn Cys Leu Asn Asn Glu Phe Asn Phe Phe Lys Arg His
            35                  40                  45
Ile Cys Asp Ala Asn Lys Glu Gly Met Phe Leu Phe Arg Ala Ala Arg
    50                  55                  60
Lys Leu Arg Gln Phe Leu Lys Met Asn Ser Thr Gly Asp Phe Asp Leu
65                  70                  75                  80
His Leu Leu Lys Val Ser Glu Gly Thr Thr Ile Leu Leu Asn Cys Thr
                85                  90                  95
Gly Gln Val Lys Gly Arg Lys Pro Ala Ala Leu Gly Glu Ala Gln Pro
                100                 105                 110
Thr Lys Ser Leu Glu Glu Asn Lys Ser Leu Lys Glu Gln Lys Lys Leu
            115                 120                 125
Asn Asp Leu Cys Phe Leu Lys Arg Leu Leu Gln Glu Ile Lys Thr Cys
    130                 135                 140
Trp Asn Lys Ile Leu Met Gly Thr Lys Glu His
145                 150                 155

<210> SEQ ID NO 20
<211> LENGTH: 156
<212> TYPE: PRT
<213> ORGANISM: Artificial Sequence
<220> FEATURE:
<223> OTHER INFORMATION: amino acid sequence of modified IL-7(MMMM)

<400> SEQUENCE: 20

Met Met Met Met Asp Cys Asp Ile Glu Gly Lys Asp Gly Lys Gln Tyr
1               5                   10                  15
Glu Ser Val Leu Met Val Ser Ile Asp Gln Leu Leu Asp Ser Met Lys
                20                  25                  30
Glu Ile Gly Ser Asn Cys Leu Asn Asn Glu Phe Asn Phe Phe Lys Arg
            35                  40                  45
His Ile Cys Asp Ala Asn Lys Glu Gly Met Phe Leu Phe Arg Ala Ala
    50                  55                  60
Arg Lys Leu Arg Gln Phe Leu Lys Met Asn Ser Thr Gly Asp Phe Asp
65                  70                  75                  80
Leu His Leu Leu Lys Val Ser Glu Gly Thr Thr Ile Leu Leu Asn Cys
                85                  90                  95
Thr Gly Gln Val Lys Gly Arg Lys Pro Ala Ala Leu Gly Glu Ala Gln
                100                 105                 110
Pro Thr Lys Ser Leu Glu Glu Asn Lys Ser Leu Lys Glu Gln Lys Lys
            115                 120                 125
Leu Asn Asp Leu Cys Phe Leu Lys Arg Leu Leu Gln Glu Ile Lys Thr
    130                 135                 140
Cys Trp Asn Lys Ile Leu Met Gly Thr Lys Glu His
145                 150                 155

<210> SEQ ID NO 21
<211> LENGTH: 398
<212> TYPE: PRT
<213> ORGANISM: Artificial Sequence
<220> FEATURE:
<223> OTHER INFORMATION: amino acid sequence of modified IL-7(M) fused
      hyFc
```

<400> SEQUENCE: 21

```
Met Asp Cys Asp Ile Glu Gly Lys Asp Gly Lys Gln Tyr Glu Ser Val
1               5                   10                  15

Leu Met Val Ser Ile Asp Gln Leu Leu Asp Ser Met Lys Glu Ile Gly
            20                  25                  30

Ser Asn Cys Leu Asn Asn Glu Phe Asn Phe Phe Lys Arg His Ile Cys
        35                  40                  45

Asp Ala Asn Lys Glu Gly Met Phe Leu Phe Arg Ala Ala Arg Lys Leu
    50                  55                  60

Arg Gln Phe Leu Lys Met Asn Ser Thr Gly Asp Phe Asp Leu His Leu
65                  70                  75                  80

Leu Lys Val Ser Glu Gly Thr Thr Ile Leu Leu Asn Cys Thr Gly Gln
                85                  90                  95

Val Lys Gly Arg Lys Pro Ala Ala Leu Gly Glu Ala Gln Pro Thr Lys
            100                 105                 110

Ser Leu Glu Glu Asn Lys Ser Leu Lys Glu Gln Lys Lys Leu Asn Asp
        115                 120                 125

Leu Cys Phe Leu Lys Arg Leu Leu Gln Glu Ile Lys Thr Cys Trp Asn
    130                 135                 140

Lys Ile Leu Met Gly Thr Lys Glu His Arg Asn Thr Gly Arg Gly Gly
145                 150                 155                 160

Glu Glu Lys Lys Lys Glu Lys Glu Lys Glu Gln Glu Glu Arg Glu
                165                 170                 175

Thr Lys Thr Pro Glu Cys Pro Ser His Thr Gln Pro Leu Gly Val Phe
            180                 185                 190

Leu Phe Pro Pro Lys Pro Lys Asp Thr Leu Met Ile Ser Arg Thr Pro
        195                 200                 205

Glu Val Thr Cys Val Val Val Asp Val Ser Gln Glu Asp Pro Glu Val
    210                 215                 220

Gln Phe Asn Trp Tyr Val Asp Gly Val Glu Val His Asn Ala Lys Thr
225                 230                 235                 240

Lys Pro Arg Glu Glu Gln Phe Asn Ser Thr Tyr Arg Val Val Ser Val
                245                 250                 255

Leu Thr Val Leu His Gln Asp Trp Leu Asn Gly Lys Glu Tyr Lys Cys
            260                 265                 270

Lys Val Ser Asn Lys Gly Leu Pro Ser Ser Ile Glu Lys Thr Ile Ser
        275                 280                 285

Lys Ala Lys Gly Gln Pro Arg Glu Pro Gln Val Tyr Thr Leu Pro Pro
    290                 295                 300

Ser Gln Glu Glu Met Thr Lys Asn Gln Val Ser Leu Thr Cys Leu Val
305                 310                 315                 320

Lys Gly Phe Tyr Pro Ser Asp Ile Ala Val Glu Trp Glu Ser Asn Gly
                325                 330                 335

Gln Pro Glu Asn Asn Tyr Lys Thr Thr Pro Pro Val Leu Asp Ser Asp
            340                 345                 350

Gly Ser Phe Phe Leu Tyr Ser Arg Leu Thr Val Asp Lys Ser Arg Trp
        355                 360                 365

Gln Glu Gly Asn Val Phe Ser Cys Ser Val Met His Glu Ala Leu His
    370                 375                 380

Asn His Tyr Thr Gln Lys Ser Leu Ser Leu Ser Leu Gly Lys
385                 390                 395
```

<210> SEQ ID NO 22

```
<211> LENGTH: 399
<212> TYPE: PRT
<213> ORGANISM: Artificial Sequence
<220> FEATURE:
<223> OTHER INFORMATION: amino acid sequence of modified IL-7(MM) fused
      hyFc

<400> SEQUENCE: 22
```

| | | | | | | | | | | | | | | |
|---|---|---|---|---|---|---|---|---|---|---|---|---|---|---|
| Met | Met | Asp | Cys | Asp | Ile | Glu | Gly | Lys | Asp | Gly | Lys | Gln | Tyr | Glu | Ser |
| 1 | | | | 5 | | | | | 10 | | | | | 15 | |

Val Leu Met Val Ser Ile Asp Gln Leu Leu Asp Ser Met Lys Glu Ile
                20                  25                  30

Gly Ser Asn Cys Leu Asn Asn Glu Phe Asn Phe Phe Lys Arg His Ile
            35                  40                  45

Cys Asp Ala Asn Lys Glu Gly Met Phe Leu Phe Arg Ala Ala Arg Lys
 50                  55                  60

Leu Arg Gln Phe Leu Lys Met Asn Ser Thr Gly Asp Phe Asp Leu His
 65                  70                  75                  80

Leu Leu Lys Val Ser Glu Gly Thr Thr Ile Leu Leu Asn Cys Thr Gly
                85                  90                  95

Gln Val Lys Gly Arg Lys Pro Ala Ala Leu Gly Glu Ala Gln Pro Thr
            100                 105                 110

Lys Ser Leu Glu Glu Asn Lys Ser Leu Lys Glu Gln Lys Lys Leu Asn
        115                 120                 125

Asp Leu Cys Phe Leu Lys Arg Leu Leu Gln Glu Ile Lys Thr Cys Trp
130                 135                 140

Asn Lys Ile Leu Met Gly Thr Lys Glu His Arg Asn Thr Gly Arg Gly
145                 150                 155                 160

Gly Glu Glu Lys Lys Lys Glu Lys Glu Lys Glu Glu Gln Glu Glu Arg
                165                 170                 175

Glu Thr Lys Thr Pro Glu Cys Pro Ser His Thr Gln Pro Leu Gly Val
            180                 185                 190

Phe Leu Phe Pro Pro Lys Pro Lys Asp Thr Leu Met Ile Ser Arg Thr
        195                 200                 205

Pro Glu Val Thr Cys Val Val Val Asp Val Ser Gln Glu Asp Pro Glu
210                 215                 220

Val Gln Phe Asn Trp Tyr Val Asp Gly Val Glu Val His Asn Ala Lys
225                 230                 235                 240

Thr Lys Pro Arg Glu Glu Gln Phe Asn Ser Thr Tyr Arg Val Val Ser
                245                 250                 255

Val Leu Thr Val Leu His Gln Asp Trp Leu Asn Gly Lys Glu Tyr Lys
            260                 265                 270

Cys Lys Val Ser Asn Lys Gly Leu Pro Ser Ser Ile Glu Lys Thr Ile
        275                 280                 285

Ser Lys Ala Lys Gly Gln Pro Arg Glu Pro Gln Val Tyr Thr Leu Pro
290                 295                 300

Pro Ser Gln Glu Glu Met Thr Lys Asn Gln Val Ser Leu Thr Cys Leu
305                 310                 315                 320

Val Lys Gly Phe Tyr Pro Ser Asp Ile Ala Val Glu Trp Glu Ser Asn
                325                 330                 335

Gly Gln Pro Glu Asn Asn Tyr Lys Thr Thr Pro Pro Val Leu Asp Ser
            340                 345                 350

Asp Gly Ser Phe Phe Leu Tyr Ser Arg Leu Thr Val Asp Lys Ser Arg
        355                 360                 365

Trp Gln Glu Gly Asn Val Phe Ser Cys Ser Val Met His Glu Ala Leu 370                 375                 380
His Asn His Tyr Thr Gln Lys Ser Leu Ser Leu Ser Leu Gly Lys
385                 390                 395

<210> SEQ ID NO 23
<211> LENGTH: 400
<212> TYPE: PRT
<213> ORGANISM: Artificial Sequence
<220> FEATURE:
<223> OTHER INFORMATION: amino acid sequence of modified IL-7(MMM) fused
      hyFc

<400> SEQUENCE: 23

Met Met Met Asp Cys Asp Ile Glu Gly Lys Asp Gly Lys Gln Tyr Glu
1               5                   10                  15

Ser Val Leu Met Val Ser Ile Asp Gln Leu Leu Asp Ser Met Lys Glu
                20                  25                  30

Ile Gly Ser Asn Cys Leu Asn Asn Glu Phe Asn Phe Phe Lys Arg His
            35                  40                  45

Ile Cys Asp Ala Asn Lys Glu Gly Met Phe Leu Phe Arg Ala Ala Arg
        50                  55                  60

Lys Leu Arg Gln Phe Leu Lys Met Asn Ser Thr Gly Asp Phe Asp Leu
65                  70                  75                  80

His Leu Leu Lys Val Ser Glu Gly Thr Thr Ile Leu Leu Asn Cys Thr
                85                  90                  95

Gly Gln Val Lys Gly Arg Lys Pro Ala Ala Leu Gly Glu Ala Gln Pro
            100                 105                 110

Thr Lys Ser Leu Glu Glu Asn Lys Ser Leu Lys Glu Gln Lys Lys Leu
        115                 120                 125

Asn Asp Leu Cys Phe Leu Lys Arg Leu Leu Gln Glu Ile Lys Thr Cys
130                 135                 140

Trp Asn Lys Ile Leu Met Gly Thr Lys Glu His Arg Asn Thr Gly Arg
145                 150                 155                 160

Gly Gly Glu Glu Lys Lys Lys Glu Lys Glu Lys Glu Gln Glu Glu
                165                 170                 175

Arg Glu Thr Lys Thr Pro Glu Cys Pro Ser His Thr Gln Pro Leu Gly
            180                 185                 190

Val Phe Leu Phe Pro Pro Lys Pro Lys Asp Thr Leu Met Ile Ser Arg
        195                 200                 205

Thr Pro Glu Val Thr Cys Val Val Val Asp Val Ser Gln Glu Asp Pro
210                 215                 220

Glu Val Gln Phe Asn Trp Tyr Val Asp Gly Val Glu Val His Asn Ala
225                 230                 235                 240

Lys Thr Lys Pro Arg Glu Glu Gln Phe Asn Ser Thr Tyr Arg Val Val
                245                 250                 255

Ser Val Leu Thr Val Leu His Gln Asp Trp Leu Asn Gly Lys Glu Tyr
            260                 265                 270

Lys Cys Lys Val Ser Asn Lys Gly Leu Pro Ser Ser Ile Glu Lys Thr
        275                 280                 285

Ile Ser Lys Ala Lys Gly Gln Pro Arg Glu Pro Gln Val Tyr Thr Leu
290                 295                 300

Pro Pro Ser Gln Glu Glu Met Thr Lys Asn Gln Val Ser Leu Thr Cys
305                 310                 315                 320

Leu Val Lys Gly Phe Tyr Pro Ser Asp Ile Ala Val Glu Trp Glu Ser
                325                 330                 335

-continued

```
Asn Gly Gln Pro Glu Asn Asn Tyr Lys Thr Thr Pro Val Leu Asp
                340                 345                 350

Ser Asp Gly Ser Phe Phe Leu Tyr Ser Arg Leu Thr Val Asp Lys Ser
            355                 360                 365

Arg Trp Gln Glu Gly Asn Val Phe Ser Cys Ser Val Met His Glu Ala
370                 375                 380

Leu His Asn His Tyr Thr Gln Lys Ser Leu Ser Leu Ser Leu Gly Lys
385                 390                 395                 400
```

<210> SEQ ID NO 24
<211> LENGTH: 400
<212> TYPE: PRT
<213> ORGANISM: Artificial Sequence
<220> FEATURE:
<223> OTHER INFORMATION: amino acid sequence of modified IL-7(MGM) fused hyFc

<400> SEQUENCE: 24

```
Met Gly Met Asp Cys Asp Ile Glu Gly Lys Asp Gly Lys Gln Tyr Glu
1               5                   10                  15

Ser Val Leu Met Val Ser Ile Asp Gln Leu Leu Asp Ser Met Lys Glu
                20                  25                  30

Ile Gly Ser Asn Cys Leu Asn Asn Glu Phe Asn Phe Phe Lys Arg His
            35                  40                  45

Ile Cys Asp Ala Asn Lys Glu Gly Met Phe Leu Phe Arg Ala Ala Arg
        50                  55                  60

Lys Leu Arg Gln Phe Leu Lys Met Asn Ser Thr Gly Asp Phe Asp Leu
65                  70                  75                  80

His Leu Leu Lys Val Ser Glu Gly Thr Thr Ile Leu Leu Asn Cys Thr
                85                  90                  95

Gly Gln Val Lys Gly Arg Lys Pro Ala Ala Leu Gly Glu Ala Gln Pro
            100                 105                 110

Thr Lys Ser Leu Glu Glu Asn Lys Ser Leu Lys Glu Gln Lys Lys Leu
        115                 120                 125

Asn Asp Leu Cys Phe Leu Lys Arg Leu Leu Gln Glu Ile Lys Thr Cys
130                 135                 140

Trp Asn Lys Ile Leu Met Gly Thr Lys Glu His Arg Asn Thr Gly Arg
145                 150                 155                 160

Gly Gly Glu Glu Lys Lys Glu Lys Glu Lys Glu Glu Gln Glu Glu
                165                 170                 175

Arg Glu Thr Lys Thr Pro Glu Cys Pro Ser His Thr Gln Pro Leu Gly
            180                 185                 190

Val Phe Leu Phe Pro Pro Lys Pro Lys Asp Thr Leu Met Ile Ser Arg
        195                 200                 205

Thr Pro Glu Val Thr Cys Val Val Val Asp Val Ser Gln Glu Asp Pro
210                 215                 220

Glu Val Gln Phe Asn Trp Tyr Val Asp Gly Val Glu Val His Asn Ala
225                 230                 235                 240

Lys Thr Lys Pro Arg Glu Glu Gln Phe Asn Ser Thr Tyr Arg Val Val
                245                 250                 255

Ser Val Leu Thr Val Leu His Gln Asp Trp Leu Asn Gly Lys Glu Tyr
            260                 265                 270

Lys Cys Lys Val Ser Asn Lys Gly Leu Pro Ser Ser Ile Glu Lys Thr
        275                 280                 285

Ile Ser Lys Ala Lys Gly Gln Pro Arg Glu Pro Gln Val Tyr Thr Leu
290                 295                 300
```

Pro Pro Ser Gln Glu Glu Met Thr Lys Asn Gln Val Ser Leu Thr Cys
305                 310                 315                 320

Leu Val Lys Gly Phe Tyr Pro Ser Asp Ile Ala Val Glu Trp Glu Ser
            325                 330                 335

Asn Gly Gln Pro Glu Asn Asn Tyr Lys Thr Thr Pro Pro Val Leu Asp
        340                 345                 350

Ser Asp Gly Ser Phe Phe Leu Tyr Ser Arg Leu Thr Val Asp Lys Ser
        355                 360                 365

Arg Trp Gln Glu Gly Asn Val Phe Ser Cys Ser Val Met His Glu Ala
    370                 375                 380

Leu His Asn His Tyr Thr Gln Lys Ser Leu Ser Leu Ser Leu Gly Lys
385                 390                 395                 400

<210> SEQ ID NO 25
<211> LENGTH: 401
<212> TYPE: PRT
<213> ORGANISM: Artificial Sequence
<220> FEATURE:
<223> OTHER INFORMATION: amino acid sequence of modified IL-7(MMMM)
    fused hyFc

<400> SEQUENCE: 25

Met Met Met Met Asp Cys Asp Ile Glu Gly Lys Asp Gly Lys Gln Tyr
1               5                   10                  15

Glu Ser Val Leu Met Val Ser Ile Asp Gln Leu Leu Asp Ser Met Lys
            20                  25                  30

Glu Ile Gly Ser Asn Cys Leu Asn Asn Glu Phe Asn Phe Phe Lys Arg
        35                  40                  45

His Ile Cys Asp Ala Asn Lys Glu Gly Met Phe Leu Phe Arg Ala Ala
    50                  55                  60

Arg Lys Leu Arg Gln Phe Leu Lys Met Asn Ser Thr Gly Asp Phe Asp
65                  70                  75                  80

Leu His Leu Leu Lys Val Ser Glu Gly Thr Thr Ile Leu Leu Asn Cys
                85                  90                  95

Thr Gly Gln Val Lys Gly Arg Lys Pro Ala Ala Leu Gly Glu Ala Gln
            100                 105                 110

Pro Thr Lys Ser Leu Glu Glu Asn Lys Ser Leu Lys Glu Gln Lys Lys
        115                 120                 125

Leu Asn Asp Leu Cys Phe Leu Lys Arg Leu Leu Gln Glu Ile Lys Thr
    130                 135                 140

Cys Trp Asn Lys Ile Leu Met Gly Thr Lys Glu His Arg Asn Thr Gly
145                 150                 155                 160

Arg Gly Gly Glu Glu Lys Lys Lys Glu Lys Glu Lys Glu Glu Gln Glu
                165                 170                 175

Glu Arg Glu Thr Lys Thr Pro Glu Cys Pro Ser His Thr Gln Pro Leu
            180                 185                 190

Gly Val Phe Leu Phe Pro Pro Lys Pro Lys Asp Thr Leu Met Ile Ser
        195                 200                 205

Arg Thr Pro Glu Val Thr Cys Val Val Val Asp Val Ser Gln Glu Asp
    210                 215                 220

Pro Glu Val Gln Phe Asn Trp Tyr Val Asp Gly Val Glu Val His Asn
225                 230                 235                 240

Ala Lys Thr Lys Pro Arg Glu Glu Gln Phe Asn Ser Thr Tyr Arg Val
                245                 250                 255

Val Ser Val Leu Thr Val Leu His Gln Asp Trp Leu Asn Gly Lys Glu

```
            260                 265                 270
Tyr Lys Cys Lys Val Ser Asn Lys Gly Leu Pro Ser Ser Ile Glu Lys
            275                 280                 285

Thr Ile Ser Lys Ala Lys Gly Gln Pro Arg Glu Pro Gln Val Tyr Thr
            290                 295                 300

Leu Pro Pro Ser Gln Glu Glu Met Thr Lys Asn Gln Val Ser Leu Thr
305                 310                 315                 320

Cys Leu Val Lys Gly Phe Tyr Pro Ser Asp Ile Ala Val Glu Trp Glu
                    325                 330                 335

Ser Asn Gly Gln Pro Glu Asn Asn Tyr Lys Thr Thr Pro Pro Val Leu
                340                 345                 350

Asp Ser Asp Gly Ser Phe Phe Leu Tyr Ser Arg Leu Thr Val Asp Lys
            355                 360                 365

Ser Arg Trp Gln Glu Gly Asn Val Phe Ser Cys Ser Val Met His Glu
            370                 375                 380

Ala Leu His Asn His Tyr Thr Gln Lys Ser Leu Ser Leu Ser Leu Gly
385                 390                 395                 400

Lys

<210> SEQ ID NO 26
<211> LENGTH: 397
<212> TYPE: PRT
<213> ORGANISM: Artificial Sequence
<220> FEATURE:
<223> OTHER INFORMATION: amino acid sequence of human IL-7 fused hyFc

<400> SEQUENCE: 26

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
                20                  25                  30

Asn Cys Leu Asn Asn Glu Phe Asn Phe Phe Lys Arg His Ile Cys Asp
            35                  40                  45

Ala Asn Lys Glu Gly Met Phe Leu Phe Arg Ala Ala Arg Lys Leu Arg
        50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His Arg Asn Thr Gly Arg Gly Gly Glu
145                 150                 155                 160

Glu Lys Lys Lys Glu Lys Glu Lys Glu Glu Gln Glu Arg Glu Thr
                165                 170                 175

Lys Thr Pro Glu Cys Pro Ser His Thr Gln Pro Leu Gly Val Phe Leu
            180                 185                 190

Phe Pro Pro Lys Pro Lys Asp Thr Leu Met Ile Ser Arg Thr Pro Glu
        195                 200                 205

Val Thr Cys Val Val Val Asp Val Ser Gln Glu Asp Pro Glu Val Gln
    210                 215                 220
```

```
Phe Asn Trp Tyr Val Asp Gly Val Glu Val His Asn Ala Lys Thr Lys
225                 230                 235                 240

Pro Arg Glu Glu Gln Phe Asn Ser Thr Tyr Arg Val Val Ser Val Leu
                245                 250                 255

Thr Val Leu His Gln Asp Trp Leu Asn Gly Lys Glu Tyr Lys Cys Lys
                260                 265                 270

Val Ser Asn Lys Gly Leu Pro Ser Ser Ile Glu Lys Thr Ile Ser Lys
            275                 280                 285

Ala Lys Gly Gln Pro Arg Glu Pro Gln Val Tyr Thr Leu Pro Pro Ser
        290                 295                 300

Gln Glu Glu Met Thr Lys Asn Gln Val Ser Leu Thr Cys Leu Val Lys
305                 310                 315                 320

Gly Phe Tyr Pro Ser Asp Ile Ala Val Glu Trp Glu Ser Asn Gly Gln
                325                 330                 335

Pro Glu Asn Asn Tyr Lys Thr Thr Pro Pro Val Leu Asp Ser Asp Gly
                340                 345                 350

Ser Phe Phe Leu Tyr Ser Arg Leu Thr Val Asp Lys Ser Arg Trp Gln
            355                 360                 365

Glu Gly Asn Val Phe Ser Cys Ser Val Met His Glu Ala Leu His Asn
        370                 375                 380

His Tyr Thr Gln Lys Ser Leu Ser Leu Ser Leu Gly Lys
385                 390                 395

<210> SEQ ID NO 27
<211> LENGTH: 395
<212> TYPE: PRT
<213> ORGANISM: Artificial Sequence
<220> FEATURE:
<223> OTHER INFORMATION: amino acid sequence of human IL-7 fused
      nonlytic mouse Fc

<400> SEQUENCE: 27

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His Ala Ser Ala Glu Pro Arg Gly Pro
145                 150                 155                 160

Thr Ile Lys Pro Cys Pro Pro Cys Lys Cys Pro Ala Pro Asn Leu Glu
                165                 170                 175

Gly Gly Pro Ser Val Phe Ile Phe Pro Pro Lys Ile Lys Asp Val Leu
```

|  |  | 180 |  |  |  | 185 |  |  |  | 190 |  |
|--|--|--|--|--|--|--|--|--|--|--|--|

Met Ile Ser Leu Ser Pro Ile Val Thr Cys Val Val Asp Val Ser
                195                 200                 205

Glu Asp Asp Pro Asp Val Gln Ile Ser Trp Phe Val Asn Asn Val Glu
210                 215                 220

Val His Thr Ala Gln Thr Gln Thr His Arg Glu Asp Tyr Asn Ser Thr
225                 230                 235                 240

Leu Arg Val Val Ser Ala Leu Pro Ile Gln His Gln Asp Trp Met Ser
                245                 250                 255

Gly Lys Ala Phe Ala Cys Ala Val Asn Asn Lys Asp Leu Pro Ala Pro
                260                 265                 270

Ile Glu Arg Thr Ile Ser Lys Pro Lys Gly Ser Val Arg Ala Pro Gln
                275                 280                 285

Val Tyr Val Leu Pro Pro Glu Glu Glu Met Thr Lys Lys Gln Val
290                 295                 300

Thr Leu Thr Cys Met Val Thr Asp Phe Met Pro Glu Asp Ile Tyr Val
305                 310                 315                 320

Glu Trp Thr Asn Asn Gly Lys Thr Glu Leu Asn Tyr Lys Asn Thr Glu
                325                 330                 335

Pro Val Leu Asp Ser Asp Gly Ser Tyr Phe Met Tyr Ser Lys Leu Arg
                340                 345                 350

Val Glu Lys Lys Asn Trp Val Glu Arg Asn Ser Tyr Ser Cys Ser Val
                355                 360                 365

Val His Glu Gly Leu His Asn His His Thr Thr Lys Ser Phe Ser Arg
370                 375                 380

Thr Pro Gly Lys Gly Gly Gly Asn Ser Gly Ser
385                 390                 395

<210> SEQ ID NO 28
<211> LENGTH: 531
<212> TYPE: DNA
<213> ORGANISM: Artificial Sequence
<220> FEATURE:
<223> OTHER INFORMATION: nucleotide sequence of human IL-7

<400> SEQUENCE: 28
atgttccacg tgagcttcag gtacatcttc ggcctgccac ccctgatcct ggtgctgctg      60
cctgtggcca gctccgactg cgacatcgag ggaaaagacg gcaagcagta cgaaagcgtg     120
ctgatggtgt ccatcgacca gctgctggat tctatgaagg agattgggag taactgcctg     180
aacaatgagt tcaacttctt caaacggcac atttgtgatg ccaacaagga gggaatgttc     240
ctgtttcggg ccgctagaaa actgaggcag ttcctgaaga tgaacagcac cggagacttt     300
gatctgcatc tgctgaaagt gtctgagggc accacaatcc tgctgaactg cactgggcag     360
gtgaaaggaa ggaagcctgc cgctctggga gaggctcagc aaccaagtc actggaggaa     420 aacaaaagcc tgaaggaaca agagaaactg aatgacctgt gctttctgaa acggctgctg     480
caggagatca aacatgttg aacaagatt ctgatgggca caaggaaca c                 531

<210> SEQ ID NO 29
<211> LENGTH: 534
<212> TYPE: DNA
<213> ORGANISM: Artificial Sequence
<220> FEATURE:
<223> OTHER INFORMATION: nucleotide sequence of modified IL-7(M)

<400> SEQUENCE: 29

```
atgttccacg tgagcttcag atacatcttc ggcctgcccc ccctgatcct ggtgctgctg    60
cccgtggcca gcagcatgga ctgcgacatc gagggcaagg acggcaagca gtacgagagc   120
gtgctgatgg tgagcatcga ccagctgctg acagcatga aggagatcgg cagcaactgc   180
ctgaacaacg agttcaactt cttcaagaga cacatctgcg acgccaacaa ggagggcatg   240
ttcctgttca gagccgccag aaagctgaga cagttcctga gatgaacag caccggcgac   300 ttcgacctgc acctgctgaa ggtgagcgag ggcacaacca tcctgctgaa ctgcaccggc   360
caggtgaagg gcagaaagcc cgccgccctg gcgaggccc agcccaccaa gagcctggag   420
gagaacaaga gcctgaagga gcagaagaag ctgaacgacc tgtgcttcct gaagagactg   480
ctgcaggaga tcaagacctg ctggaacaag atcctgatgg gcaccaagga gcac         534
```

<210> SEQ ID NO 30
<211> LENGTH: 537
<212> TYPE: DNA
<213> ORGANISM: Artificial Sequence
<220> FEATURE:
<223> OTHER INFORMATION: nucleotide sequence of modified IL-7(MM)

<400> SEQUENCE: 30

```
atgttccacg tgagcttcag atacatcttc ggcctgcccc ccctgatcct ggtgctgctg    60
cccgtggcca gcagcatgat ggactgcgac atcgagggca aggacggcaa gcagtacgag   120
agcgtgctga tggtgagcat cgaccagctg ctggacagca tgaaggagat cggcagcaac   180
tgcctgaaca acgagttcaa cttcttcaag agacacatct gcgacgccaa caaggagggc   240
atgttcctgt tcagagccgc cagaaagctg agacagttcc tgaagatgaa cagcaccggc   300
gacttcgacc tgcacctgct gaaggtgagc gagggcacaa ccatcctgct gaactgcacc   360
ggccaggtga agggcagaaa gcccgccgcc ctgggcgagg cccagcccac caagagcctg   420
gaggagaaca agagcctgaa ggagcagaag aagctgaacg acctgtgctt cctgaagaga   480
ctgctgcagg agatcaagac ctgctggaac aagatcctga tgggcaccaa ggagcac      537
```

<210> SEQ ID NO 31
<211> LENGTH: 540
<212> TYPE: DNA
<213> ORGANISM: Artificial Sequence
<220> FEATURE:
<223> OTHER INFORMATION: nucleotide sequence of modified IL-7(MMM)

<400> SEQUENCE: 31

```
atgttccacg tgagcttcag atacatcttc ggcctgcccc ccctgatcct ggtgctgctg    60
cccgtggcca gcagcatgat gatggactgc gacatcgagg gcaaggacgg caagcagtac   120
gagagcgtgc tgatggtgag catcgaccag ctgctggaca gcatgaagga gatcggcagc   180
aactgcctga caacgagtt caacttcttc aagagacaca tctgcgacgc caacaaggag   240
ggcatgttcc tgttcagagc cgccagaaag ctgagacagt tcctgaagat gaacagcacc   300
ggcgacttcg acctgcacct gctgaaggtg agcgagggca aaccatcct gctgaactgc   360 accggccagg tgaagggcag aaagcccgcc gccctgggcg aggcccagcc caccaagagc   420
ctggaggaga caagagcct gaaggagcag aagaagctga acgacctgtg cttcctgaag   480
agactgctgc aggagatcaa gacctgctgg aacaagatcc tgatgggcac caaggagcac   540
```

<210> SEQ ID NO 32
<211> LENGTH: 540
<212> TYPE: DNA
<213> ORGANISM: Artificial Sequence

```
<220> FEATURE:
<223> OTHER INFORMATION: nucleotide sequence of modified IL-7(MGM)

<400> SEQUENCE: 32
atgttccacg tgagcttcag gtacatcttc ggcctgccac ccctgatcct ggtgctgctg      60
cctgtggcca gctccatggg gatggactgc gacatcgagg aaaagacggg caagcagtac     120
gaaagcgtgc tgatggtgtc catcgaccag ctgctggatt ctatgaagga gattgggagt     180
aactgcctga caatgagtt caacttcttc aaacggcaca tttgtgatgc aacaaggag       240 ggaatgttcc tgtttcgggc cgctagaaaa ctgaggcagt tcctgaagat aacagcacc      300 ggagactttg atctgcatct gctgaaagtg tctgagggca ccacaatcct gctgaactgc     360
actgggcagg tgaaaggaag gaagcctgcc gctctgggag aggctcagcc aaccaagtca     420
ctggaggaaa acaaaagcct gaaggaacag aagaaactga tgacctgtg ctttctgaaa      480 cggctgctgc aggagatcaa acatgttgg aacaagattc tgatgggcac caaggagcac     540

<210> SEQ ID NO 33
<211> LENGTH: 540
<212> TYPE: DNA
<213> ORGANISM: Artificial Sequence
<220> FEATURE:
<223> OTHER INFORMATION: nucleotide sequence of modified IL-7(DDD)

<400> SEQUENCE: 33
atgttccacg tgagcttcag atacatcttc ggcctgcccc ccctgatcct ggtgctgctg      60
cccgtggcca gcagcgacga tgacgactgc gacatcgagg gcaaggacgg caagcagtac     120
gagagcgtgc tgatggtgag catcgaccag ctgctggaca gcatgaagga gatcggcagc     180
aactgcctga caacgagtt caacttcttc aagagacaca tctgcgacgc caacaaggag      240
ggcatgttcc tgttcagagc cgccagaaag ctgagacagt tcctgaagat aacagcacc      300 ggcgacttcg acctgcacct gctgaaggtg agcgaggca caaccatcct gctgaactgc      360
accggccagg tgaagggcag aaagcccgcc gccctgggcg aggcccagcc caccaagagc     420
ctggaggaga acaagagcct gaaggagcag aagaagctga cgacctgtg cttcctgaag     480 agactgctgc aggagatcaa gacctgctgg aacaagatcc tgatgggcac caaggagcac     540

<210> SEQ ID NO 34
<211> LENGTH: 543
<212> TYPE: DNA
<213> ORGANISM: Artificial Sequence
<220> FEATURE:
<223> OTHER INFORMATION: nucleotide sequence of modified IL-7(MMMM)

<400> SEQUENCE: 34
atgttccacg tgagcttcag atacatcttc ggcctgcccc ccctgatcct ggtgctgctg      60
cccgtggcca gcagcatgat gatgatggac tgcgacatcg agggcaagga cggcaagcag     120
tacgagagcg tgctgatggt gagcatcgac cagctgctgg acagcatgaa ggagatcggc     180
agcaactgcc tgaacaacga gttcaacttc ttcaagagac acatctgcga cgccaacaag     240
gagggcatgt tcctgttcag agccgccaga aagctgagac agttcctgaa gatgaacagc     300
accggcgact tcgacctgca cctgctgaag gtgagcgagg cacaaccat cctgctgaac      360 tgcaccggcc aggtgaaggg cagaaagccc gccgccctgg gcgaggccca gcccaccaag     420
agcctggagg agaacaagag cctgaaggag cagaagaagc tgaacgacct gtgcttcctg     480
aagagactgc tgcaggagat caagacctgc tggaacaaga tcctgatggg caccaaggag     540
```

<210> SEQ ID NO 35
<211> LENGTH: 1284
<212> TYPE: DNA
<213> ORGANISM: Artificial Sequence
<220> FEATURE:
<223> OTHER INFORMATION: nucleotide sequence of modified IL-7(M) fused hyFc

<400> SEQUENCE: 35

```
atgttccacg tgagcttcag atacatcttc ggcctgcccc ccctgatcct ggtgctgctg      60
cccgtggcca gcagcatgga ctgcgacatc gagggcaagg acggcaagca gtacgagagc     120
gtgctgatgg tgagcatcga ccagctgctg acagcatga aggagatcgg cagcaactgc     180
ctgaacaacg agttcaactt cttcaagaga cacatctgcg acgccaacaa ggagggcatg     240
ttcctgttca gagccgccag aaagctgaga cagttcctga gatgaacag caccggcgac     300
ttcgacctgc acctgctgaa ggtgagcgag ggcacaacca tcctgctgaa ctgcaccggc     360
caggtgaagg gcagaaagcc cgccgccctg gcgaggccc agcccaccaa gagcctggag     420
gagaacaaga gcctgaagga gcagaagaag ctgaacgacc tgtgcttcct gaagagactg     480
ctgcaggaga tcaagacctg ctggaacaag atcctgatgg gcaccaagga gcacaggaac     540
acaggcagag gcggcgagga gaagaagaag gagaaggaga aggaggagca ggaggaaaga     600
gagaccaaga cccccgagtg ccccagccac acccagcccc tgggcgtgtt cctgttccct     660
cccaagccca aggacaccct gatgatcagc agaacccccg aggtgacctg cgtggtcgtg     720
gatgtgagcc aggaagatcc cgaagtgcag ttcaactggt acgtggatgg cgtggaagtg     780
cacaacgcca agaccaagcc cagagaagag cagttcaact ccacctacag agtggtgagc     840
gtgctgaccg tgctgcacca ggactggctg aacggcaagg agtacaagtg caaggtgtcc     900
aacaaaggcc tgcccagctc catcgagaag accatcagca agccaaagg ccagcccaga     960
gaaccccagg tgtacaccct gcctcccagc caggaagaga tgaccaagaa ccaggtgtcc    1020
ctgacctgcc tggtgaaagg cttctacccc agcgacatcg ccgtggagtg ggaaagcaac    1080
ggccagcccg agaacaatta caagacaacc cctcccgtgc tggatagcga tggcagcttc    1140
tttctgtaca gcagactgac cgtggacaag agcagatggc aggaaggcaa cgtgttcagc    1200
tgcagcgtga tgcacgaagc cctgcacaac cactacaccc agaagagcct gtccctgagc    1260
ctgggcaagt gactcgagtc taga                                            1284
```

<210> SEQ ID NO 36
<211> LENGTH: 1272
<212> TYPE: DNA
<213> ORGANISM: Artificial Sequence
<220> FEATURE:
<223> OTHER INFORMATION: nucleotide sequence of modified IL-7(MM) fused hyFc

<400> SEQUENCE: 36

```
atgttccacg tgagcttcag atacatcttc ggcctgcccc ccctgatcct ggtgctgctg      60
cccgtggcca gcagcatgat ggactgcgac atcgagggca aggacggcaa gcagtacgag     120
agcgtgctga tggtgagcat cgaccagctg ctggacagca tgaaggagat cggcagcaac     180
tgcctgaaca acgagttcaa cttcttcaag agacacatct gcgacgccaa caaggagggc     240
atgttcctgt tcagagccgc cagaaagctg agacagttcc tgaagatgaa cagcaccggc     300
gacttcgacc tgcacctgct gaaggtgagc gagggcacaa ccatcctgct gaactgcacc     360
```

```
ggccaggtga agggcagaaa gcccgccgcc ctgggcgagg cccagcccac caagagcctg    420
gaggagaaca agagcctgaa ggagcagaag aagctgaacg acctgtgctt cctgaagaga    480
ctgctgcagg agatcaagac ctgctggaac aagatcctga tgggcaccaa ggagcacagg    540
aacacaggca gaggcggcga ggagaagaag aaggagaagg agaaggagga gcaggaggaa    600
agagagacca agaccccccga gtgcccagc cacacccagc ccctgggcgt gttcctgttc    660
cctcccaagc ccaaggacac cctgatgatc agcagaaccc ccgaggtgac ctgcgtggtc    720
gtggatgtga gccaggaaga tcccgaagtg cagttcaact ggtacgtgga tggcgtggaa    780
gtgcacaacg ccaagaccaa gcccagagaa gagcagttca actccaccta cagagtggtg    840
agcgtgctga ccgtgctgca ccaggactgg ctgaacggca aggagtacaa gtgcaaggtg    900
tccaacaaag gcctgcccag ctccatcgag aagaccatca gcaaagccaa aggccagccc    960
agagaacccc aggtgtacac cctgcctccc agccaggaag gatgaccaa gaaccaggtg   1020 tccctgacct gcctggtgaa aggcttctac cccagcgaca tcgccgtgga gtgggaaagc   1080
aacggccagc ccgagaacaa ttacaagaca ccccctcccg tgctggatag cgatggcagc   1140
ttctttctgt acagcagact gaccgtggac aagagcagat ggcaggaagg caacgtgttc   1200
agctgcagcg tgatgcacga agccctgcac aaccactaca cccagaagag cctgtccctg   1260
agcctgggca ag                                                       1272

<210> SEQ ID NO 37
<211> LENGTH: 1275
<212> TYPE: DNA
<213> ORGANISM: Artificial Sequence
<220> FEATURE:
<223> OTHER INFORMATION: nucleotide sequence of modified IL-7(MMM) fused
      hyFc

<400> SEQUENCE: 37
atgttccacg tgagcttcag atacatcttc ggcctgcccc ccctgatcct ggtgctgctg     60
cccgtggcca gcagcatgat gatggactgc gacatcgagg gcaaggacgg caagcagtac    120
gagagcgtgc tgatggtgag catcgaccag ctgctggaca gcatgaagga gatcggcagc    180
aactgcctga acaacgagtt caacttcttc aagagacaca tctgcgacgc caacaaggag    240
ggcatgttcc tgttcagagc cgccagaaag ctgagacagt tcctgaagat gaacagcacc    300
ggcgacttcg acctgcacct gctgaaggtg agcgagggca caaccatcct gctgaactgc    360
accggccagg tgaagggcag aaagcccgcc gccctgggcg aggcccagcc caccaagagc    420
ctggaggaga caagagcct gaaggagcag aagaagctga cgacctgtg cttcctgaag    480 agactgctgc aggagatcaa gacctgctgg aacaagatcc tgatgggcac caaggagcac    540
aggaacacag gcagaggcgg cgaggagaag aaggagaagg agaaggagga ggagcaggag    600
gaaagagaga ccaagacccc cgagtgcccc agccacaccc agcccctggg cgtgttcctg    660
ttccctccca gcccaagga caccctgatg atcagcagaa ccccgaggt gacctgcgtg    720 gtcgtggatg tgagccagga agatcccgaa gtgcagttca actggtacgt ggatggcgtg    780
gaagtgcaca acgccaagac caagcccaga gaagagcagt tcaactccac ctacagagtg    840
gtgagcgtgc tgaccgtgct gcaccaggac tggctgaacg gcaaggagta caagtgcaag    900
gtgtccaaca aaggcctgcc cagctccatc gagaagacca tcagcaaagc caaaggccag    960
cccagagaac cccaggtgta cacctgcct cccagccagg aagagatgac caagaaccag   1020
gtgtccctga cctgcctggt gaaaggcttc taccccagcg acatcgccgt ggagtgggaa   1080
```

```
agcaacggcc agcccgagaa caattacaag acaacccctc ccgtgctgga tagcgatggc    1140
agcttctttc tgtacagcag actgaccgtg acaagagca gatggcagga aggcaacgtg     1200
ttcagctgca gcgtgatgca cgaagccctg cacaaccact acacccagaa gagcctgtcc    1260
ctgagcctgg gcaag                                                     1275
```

<210> SEQ ID NO 38
<211> LENGTH: 1275
<212> TYPE: DNA
<213> ORGANISM: Artificial Sequence
<220> FEATURE:
<223> OTHER INFORMATION: nucleotide sequence of modified IL-7(MGM) fused
      hyFc

<400> SEQUENCE: 38

```
atgttccacg tgagcttcag gtacatcttc ggcctgccac ccctgatcct ggtgctgctg     60
cctgtggcca gctccatggg gatggactgc gacatcgagg gaaaagacgg caagcagtac    120
gaaagcgtgc tgatggtgtc catcgaccag ctgctggatt ctatgaagga gattgggagt    180
aactgcctga caatgagtt caacttcttc aaacggcaca tttgtgatgc caacaaggag    240
ggaatgttcc tgtttcgggc cgctagaaaa ctgaggcagt cctgaagat gaacagcacc    300 ggagactttg atctgcatct gctgaaagtg tctgagggca ccacaatcct gctgaactgc    360
actgggcagg tgaaaggaag gaagcctgcc gctctgggag aggctcagcc aaccaagtca    420
ctggaggaaa acaaaagcct gaaggaacag aagaaactga atgacctgtg ctttctgaaa    480
cggctgctgc aggagatcaa acatgttgg aacaagattc tgatgggcac aaaggaacac    540
cgcaatactg gcggggcgg ggaggaaaag aaaaaggaga aggaaaagga ggaacaggag    600
gaaagagaga ctaagacccc agaatgtccc agccatactc agccctggg ggtgttcctg    660 tttcccccta aacctaagga taccctgatg atcagcagga caccggaggt gacctgcgtg    720
gtcgtggatg tgagccagga agatcccgaa gtgcagttca actggtacgt ggatggcgtg    780
gaagtgcaca acgccaagac caagcccaga gaagagcagt tcaactccac ctacagagtg    840
gtgagcgtgc tgaccgtgct gcaccaggac tggctgaacg gcaaggagta caagtgcaag    900
gtgtccaaca aaggcctgcc cagctccatc gagaagacca tcagcaaagc caaggccag    960 cccagagaac cccaggtgta cacctgcct cccagccagg aagagatgac caagaaccag    1020
gtgtccctga cctgcctggt gaaaggcttc taccccagcg acatcgccgt ggagtgggaa    1080
agcaacggcc agcccgagaa caattacaag acaacccctc ccgtgctgga tagcgatggc    1140
agcttctttc tgtacagcag actgaccgtg acaagagca gatggcagga aggcaacgtg    1200
ttcagctgca gcgtgatgca cgaagccctg cacaaccact acacccagaa gagcctgtcc    1260
ctgagcctgg gcaag                                                    1275
```

<210> SEQ ID NO 39
<211> LENGTH: 1278
<212> TYPE: DNA
<213> ORGANISM: Artificial Sequence
<220> FEATURE:
<223> OTHER INFORMATION: nucleotide sequence of modified IL-7(MMMM)
      fused hyFc

<400> SEQUENCE: 39

```
atgttccacg tgagcttcag atacatcttc ggcctgcccc ccctgatcct ggtgctgctg     60
cccgtggcca gcagcatgat gatgatggac tgcgacatcg agggcaagga cggcaagcag    120
```

| | |
|---|---|
| tacgagagcg tgctgatggt gagcatcgac cagctgctgg acagcatgaa ggagatcggc | 180 |
| agcaactgcc tgaacaacga gttcaacttc ttcaagagac acatctgcga cgccaacaag | 240 |
| gagggcatgt tcctgttcag agccgccaga aagctgagac agttcctgaa gatgaacagc | 300 |
| accggcgact tcgacctgca cctgctgaag gtgagcgagg gcacaaccat cctgctgaac | 360 |
| tgcaccggcc aggtgaaggg cagaaagccc gccgccctgg gcgaggccca gcccaccaag | 420 |
| agcctggagg agaacaagag cctgaaggag cagaagaagc tgaacgacct gtgcttcctg | 480 |
| aagagactgc tgcaggagat caagacctgc tggaacaaga tcctgatggg caccaaggag | 540 |
| cacaggaaca caggcagagg cggcgaggag aagaagaagg agaaggagaa ggaggagcag | 600 |
| gaggaaagag agaccaagac ccccgagtgc cccagccaca cccagcccct gggcgtgttc | 660 |
| ctgttccctc ccaagcccaa ggacaccctg atgatcagca gaacccccga ggtgacctgc | 720 |
| gtggtcgtgg atgtgagcca ggaagatccc gaagtgcagt tcaactggta cgtggatggc | 780 |
| gtggaagtgc acaacgccaa gaccaagccc agagaagagc agttcaactc cacctacaga | 840 |
| gtggtgagcg tgctgaccgt gctgcaccag gactggctga acggcaagga gtacaagtgc | 900 |
| aaggtgtcca acaaaggcct gcccagctcc atcgagaaga ccatcagcaa agccaaaggc | 960 |
| cagcccagag aaccccaggt gtacaccctg cctcccagcc aggaagagat gaccaagaac | 1020 |
| caggtgtccc tgacctgcct ggtgaaaggc ttctacccca gcgacatcgc cgtggagtgg | 1080 |
| gaaagcaacg gccagcccga gaacaattac aagacaaccc ctcccgtgct ggatagcgat | 1140 |
| ggcagcttct ttctgtacag cagactgacc gtggacaaga gcagatggca ggaaggcaac | 1200 |
| gtgttcagct gcagcgtgat gcacgaagcc ctgcacaacc actacaccca gaagagcctg | 1260 |
| tccctgagcc tgggcaag | 1278 |

```
<210> SEQ ID NO 40
<211> LENGTH: 4
<212> TYPE: PRT
<213> ORGANISM: Artificial Sequence
<220> FEATURE:
<223> OTHER INFORMATION: oligopeptides conjugated with IL-7

<400> SEQUENCE: 40

Met Met Met Met
1

<210> SEQ ID NO 41
<211> LENGTH: 20
<212> TYPE: DNA
<213> ORGANISM: Artificial Sequence
<220> FEATURE:
<223> OTHER INFORMATION: Forward primer for detecting NS-1 gene

<400> SEQUENCE: 41
tgcgggaaag cagatagtgg                                                   20

<210> SEQ ID NO 42
<211> LENGTH: 20
<212> TYPE: DNA
<213> ORGANISM: Artificial Sequence
<220> FEATURE:
<223> OTHER INFORMATION: Reverse primer for detecting NS-1 gene

<400> SEQUENCE: 42
tcagttaggt agcgcgaagc                                                   20

<210> SEQ ID NO 43
```

```
<211> LENGTH: 18
<212> TYPE: DNA
<213> ORGANISM: Artificial Sequence
<220> FEATURE:
<223> OTHER INFORMATION: Forward primer for detecting L32 gene

<400> SEQUENCE: 43
gaaactggcg gaaaccca                                              18

<210> SEQ ID NO 44
<211> LENGTH: 20
<212> TYPE: DNA
<213> ORGANISM: Artificial Sequence
<220> FEATURE:
<223> OTHER INFORMATION: Reverse primer for detecting L32 gene

<400> SEQUENCE: 44
ggatctggcc cttgaacctt                                            20
```